United States Patent [19]
Green et al.

[11] Patent Number: 5,292,326
[45] Date of Patent: Mar. 8, 1994

[54] APPARATUS AND METHOD FOR SUBCUTICULAR STAPLING OF BODY TISSUE

[75] Inventors: David T. Green, Westport; Henry Bolanos, East Norwalk; Diego Fontayne, Norwalk; Henry Sienkiewicz, Stamford, all of Conn.

[73] Assignee: United States Surgical Corporation, Norwalk, Conn.

[21] Appl. No.: 842,448

[22] Filed: Feb. 27, 1992

Related U.S. Application Data

[63] Continuation-in-part of Ser. No. 581,776, Sep. 13, 1990, and a continuation-in-part of Ser. No. 630,224, Dec. 19, 1990.

[51] Int. Cl.$^5$ ............................................. A61B 17/00
[52] U.S. Cl. .................................... 606/143; 606/142; 606/213; 606/219; 227/181
[58] Field of Search ..................... 606/142–219, 606/221; 227/175–181

[56] References Cited

U.S. PATENT DOCUMENTS

2,182    7/1841   Ballard .
415,175  11/1889  Prouty .
715,612  12/1902  Van Schott .
816,026  3/1906   Meier .

(List continued on next page.)

FOREIGN PATENT DOCUMENTS

256506   5/1963   Australia .
0173451  3/1986   European Pat. Off. .
0392750  10/1990  European Pat. Off. .
2740274  3/1978   Fed. Rep. of Germany .
8522122  10/1985  Fed. Rep. of Germany .
2308349  11/1976  France .
8503857  9/1985   PCT Int'l Appl. .
8901767  3/1989   PCT Int'l Appl. .
166352   3/1984   Switzerland .
888965   12/1981  U.S.S.R. .
1210801  2/1986   U.S.S.R. .

873960   8/1961   United Kingdom .
1172775  12/1969  United Kingdom .
1350100  4/1974   United Kingdom .

OTHER PUBLICATIONS

"United States Surgical Corporation Information Booklet for Auto Suture ® Purse String Insturment", copyright 1977, 1978, United States Surgical Corporation.
Publication entitled "Wound Repair", Erle E. Peacock, pp. 141–158, dated 1984.
Publication entitled "La Sutura Perde Il Filo".
European Appln. No. 0 477 619 A1 Search Report.

*Primary Examiner*—Stephen C. Pellegrino
*Assistant Examiner*—Gary Jackson

[57] ABSTRACT

A surgical apparatus for attaching two portions of cutaneous body tissue includes a pair of opposed elongated jaws having members thereon at one end and which are movable toward each other to a closed position to engage two body tissue portions positioned within the members to move the bodily tissue portions into close approximation. Manually gripping systems of several alternative configurations are provided to actuate a mechanical transmission system to close the jaws. In a preferred embodiment, a fork is movable from a first position to a second position by manually operable devices to move the jaws toward each other. A pair of cam faces is located adjacent the opposite ends of the jaws. As the fork moves to its second position, the tines of the fork engage against the cam faces to move the opposed jaws to their closed position. A plurality of rod-like fasteners are carried in a stacked configuration proximally of the jaws such that when the jaws are in their closed position and the two body tissue portions are held in close approximation, each rod-like fastener is movable to a position of ingress to penetrate the body tissue portions to attach the two body tissue portions together. A method of attaching cutaneous body tissue portions is also disclosed.

44 Claims, 18 Drawing Sheets

U.S. PATENT DOCUMENTS

| | | |
|---|---|---|
| 1,200,594 | 10/1916 | Curtis . |
| 1,452,373 | 4/1923 | Gomez . |
| 1,906,527 | 5/1933 | Bradley . |
| 1,933,317 | 10/1933 | Curtis . |
| 2,254,620 | 9/1941 | Miller . |
| 2,356,376 | 8/1944 | Brown . |
| 2,668,538 | 2/1954 | Baker . |
| 2,811,971 | 11/1957 | Scott . |
| 2,910,067 | 10/1959 | White . |
| 3,110,899 | 11/1963 | Warren . |
| 3,150,379 | 9/1964 | Brown . |
| 3,203,220 | 8/1965 | Kaepernick . |
| 3,205,757 | 9/1965 | Kuennen . |
| 3,378,010 | 4/1968 | Codling et al. . |
| 3,618,447 | 11/1971 | Goins . |
| 3,631,707 | 1/1972 | Miller . |
| 3,716,058 | 2/1973 | Tanner, Jr. . |
| 4,052,988 | 10/1977 | Doddi et al. . |
| 4,064,881 | 12/1977 | Meredith . |
| 4,162,678 | 7/1979 | Fedotov et al. . |
| 4,164,225 | 8/1979 | Johnson et al. . |
| 4,256,251 | 3/1981 | Moshofsky . |
| 4,345,600 | 8/1982 | Rothfuss . |
| 4,399,810 | 8/1983 | Samuels et al. . |
| 4,448,194 | 5/1984 | DiGiovanni et al. . |
| 4,493,322 | 1/1985 | Becht . |
| 4,506,669 | 3/1985 | Blake, III . |
| 4,523,591 | 6/1985 | Kaplan et al. . |
| 4,523,695 | 6/1985 | Braun et al. . |
| 4,526,173 | 7/1985 | Sheehan . |
| 4,527,725 | 7/1985 | Foslien . |
| 4,535,772 | 8/1985 | Sheehan . |
| 4,595,007 | 6/1986 | Mericle . |
| 4,610,251 | 9/1986 | Kumar . |
| 4,612,923 | 9/1986 | Kronenthal . |
| 4,688,560 | 8/1987 | Schulz . |
| 4,712,550 | 12/1987 | Sinnett . |
| 4,744,365 | 5/1988 | Kaplan et al. . |
| 4,753,636 | 6/1988 | Free . |
| 4,815,468 | 3/1989 | Annand . |
| 4,832,026 | 5/1989 | Jones . |
| 4,834,098 | 5/1989 | Jones . |
| 4,841,960 | 6/1989 | Garner . |
| 4,858,603 | 8/1989 | Clemow et al. . |
| 4,865,032 | 9/1989 | Jones . |
| 4,869,242 | 9/1989 | Galluzzo . |
| 4,873,976 | 10/1989 | Schreiber . |
| 4,874,122 | 10/1989 | Froehlich et al. . |
| 4,887,756 | 12/1989 | Puchy . |
| 4,895,148 | 1/1990 | Bays et al. . |
| 4,898,186 | 2/1990 | Ikada et al. . |
| 4,899,745 | 2/1990 | Laboureau et al. . |
| 4,924,866 | 5/1990 | Yoon . |
| 4,944,742 | 7/1990 | Clemow et al. . |
| 4,973,211 | 11/1990 | Potucek . |
| 4,976,686 | 12/1990 | Ball et al. . |
| 5,004,469 | 4/1991 | Palmieri et al. . |
| 5,007,921 | 4/1991 | Brown . |
| 5,026,374 | 6/1991 | Dezza et al. ............................ 606/73 |
| 5,047,047 | 9/1991 | Yoon . |
| 5,156,609 | 10/1992 | Nakao et al. ......................... 606/142 |
| 5,158,566 | 10/1992 | Pianetti ................................ 606/216 |

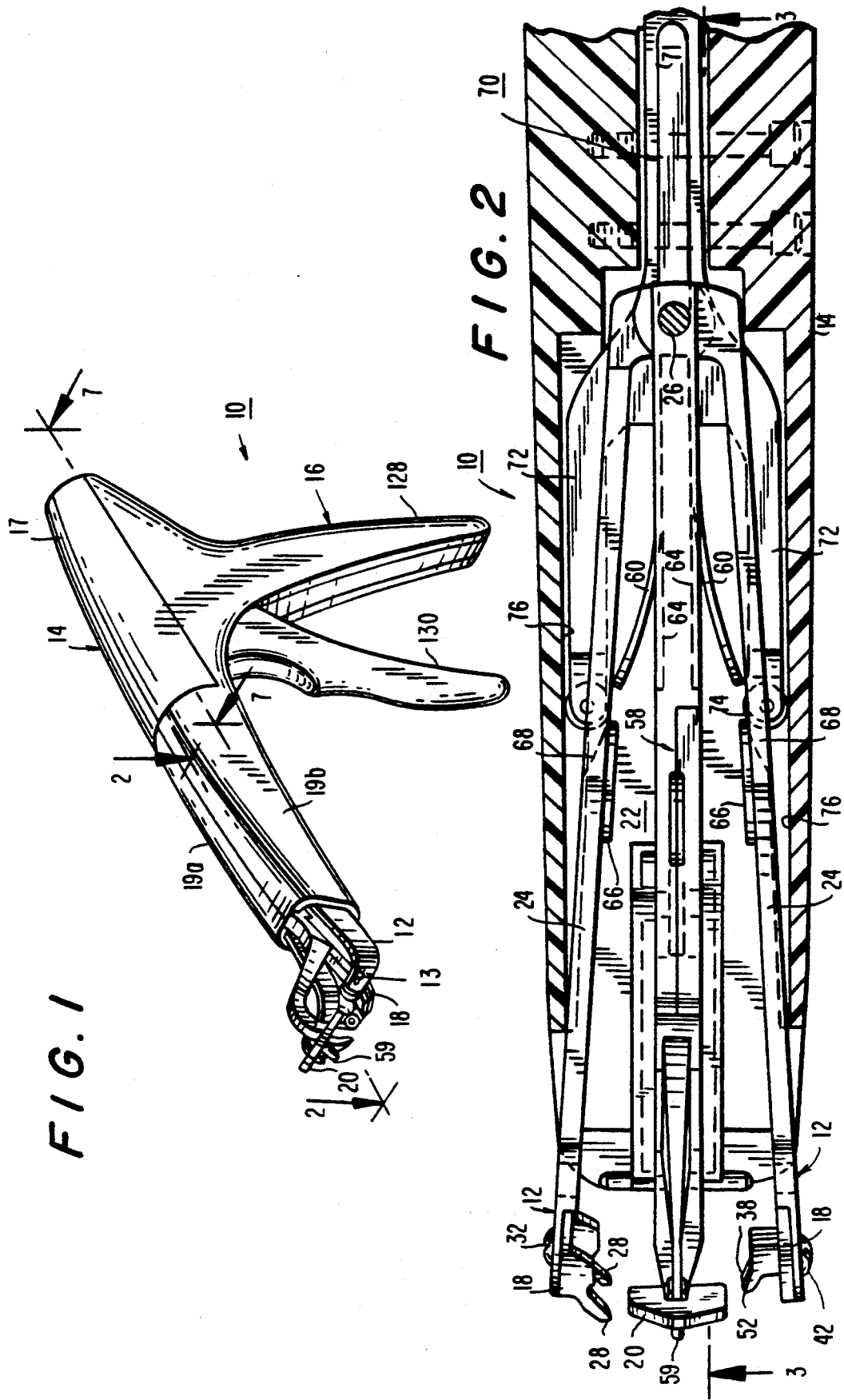

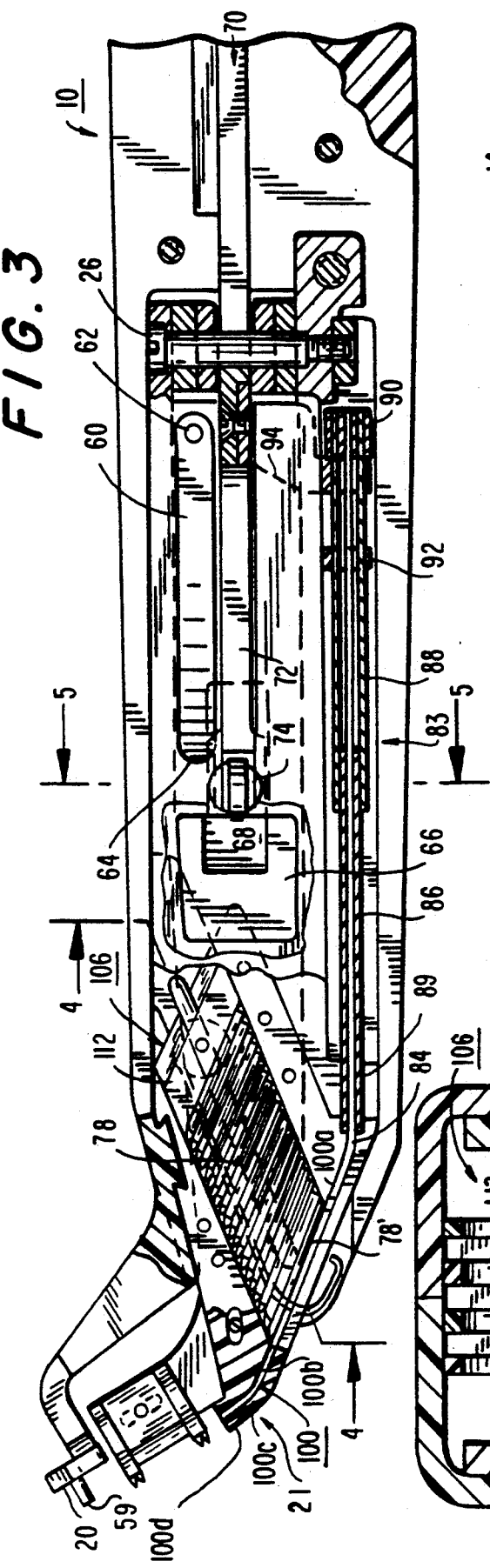

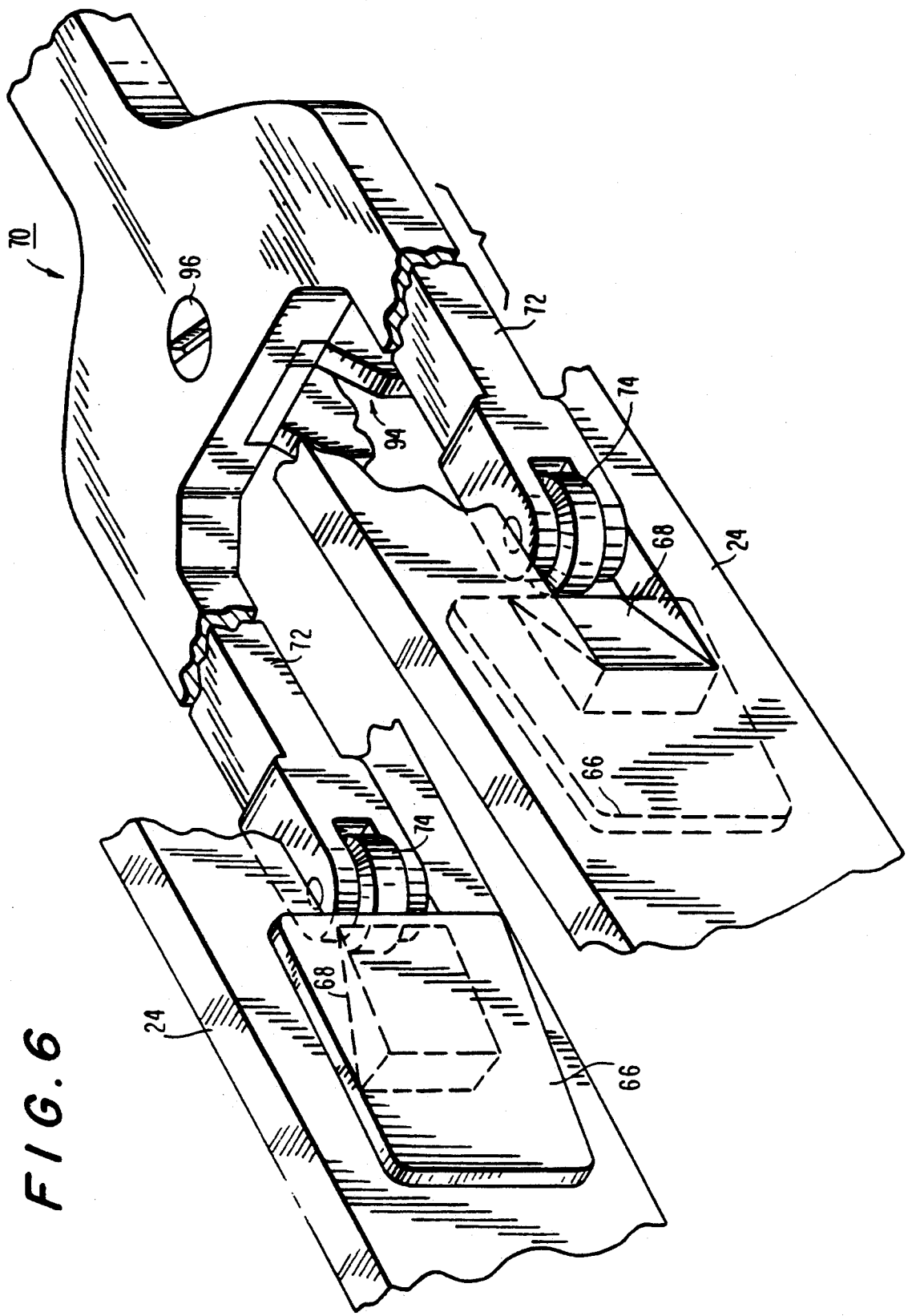

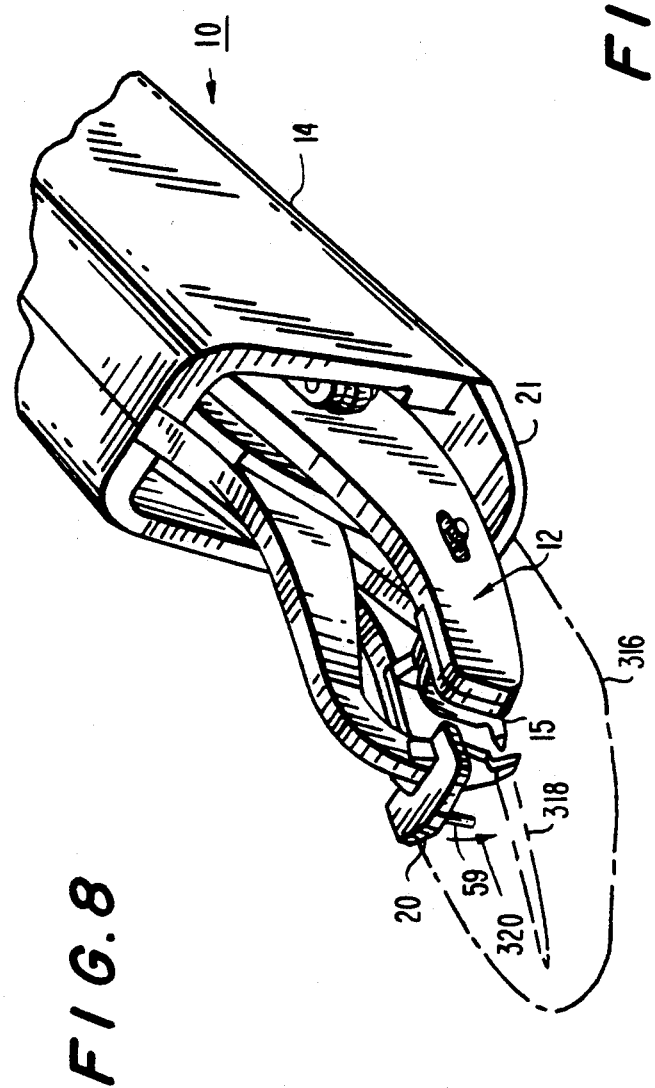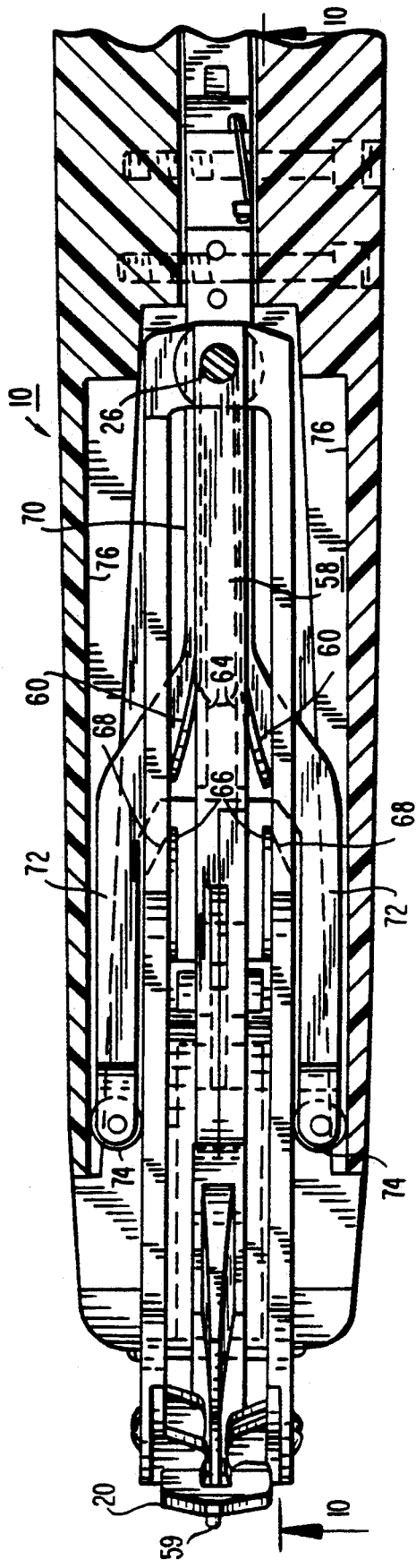

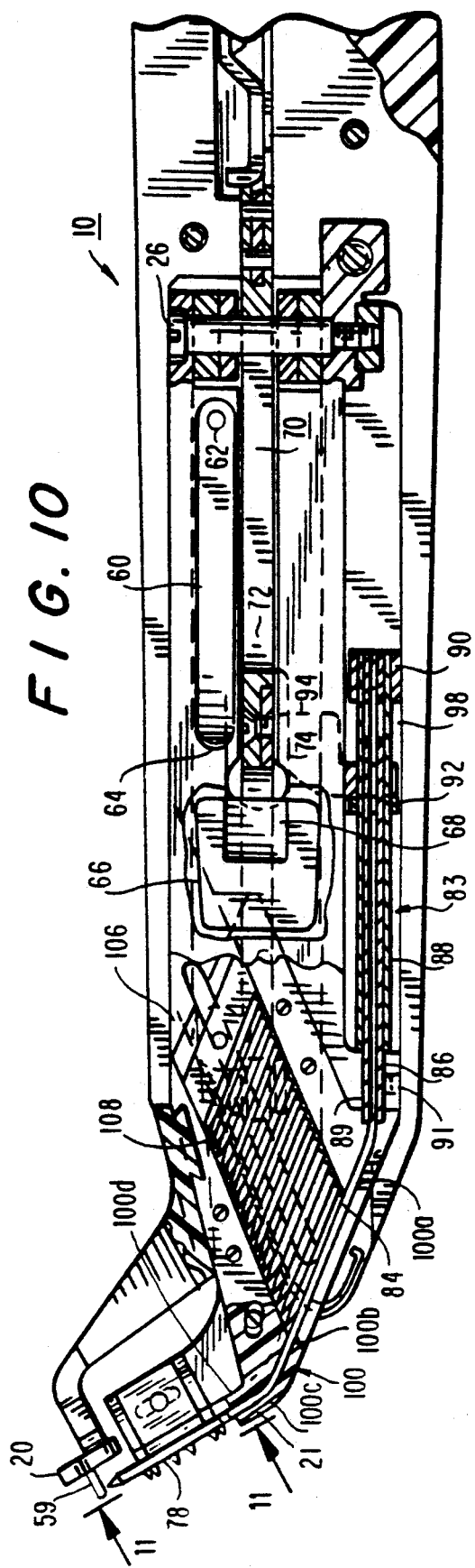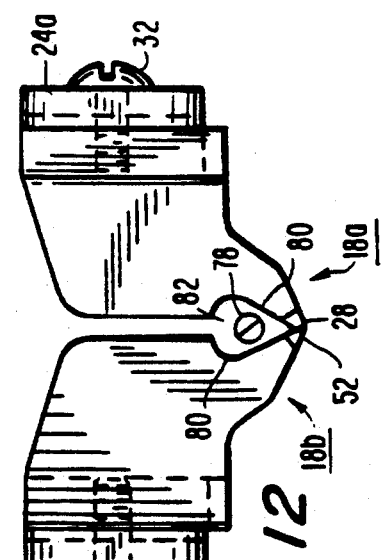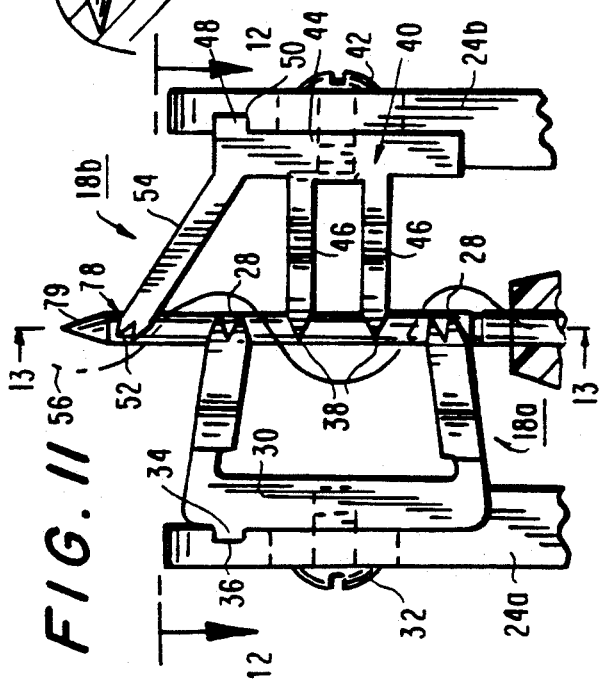

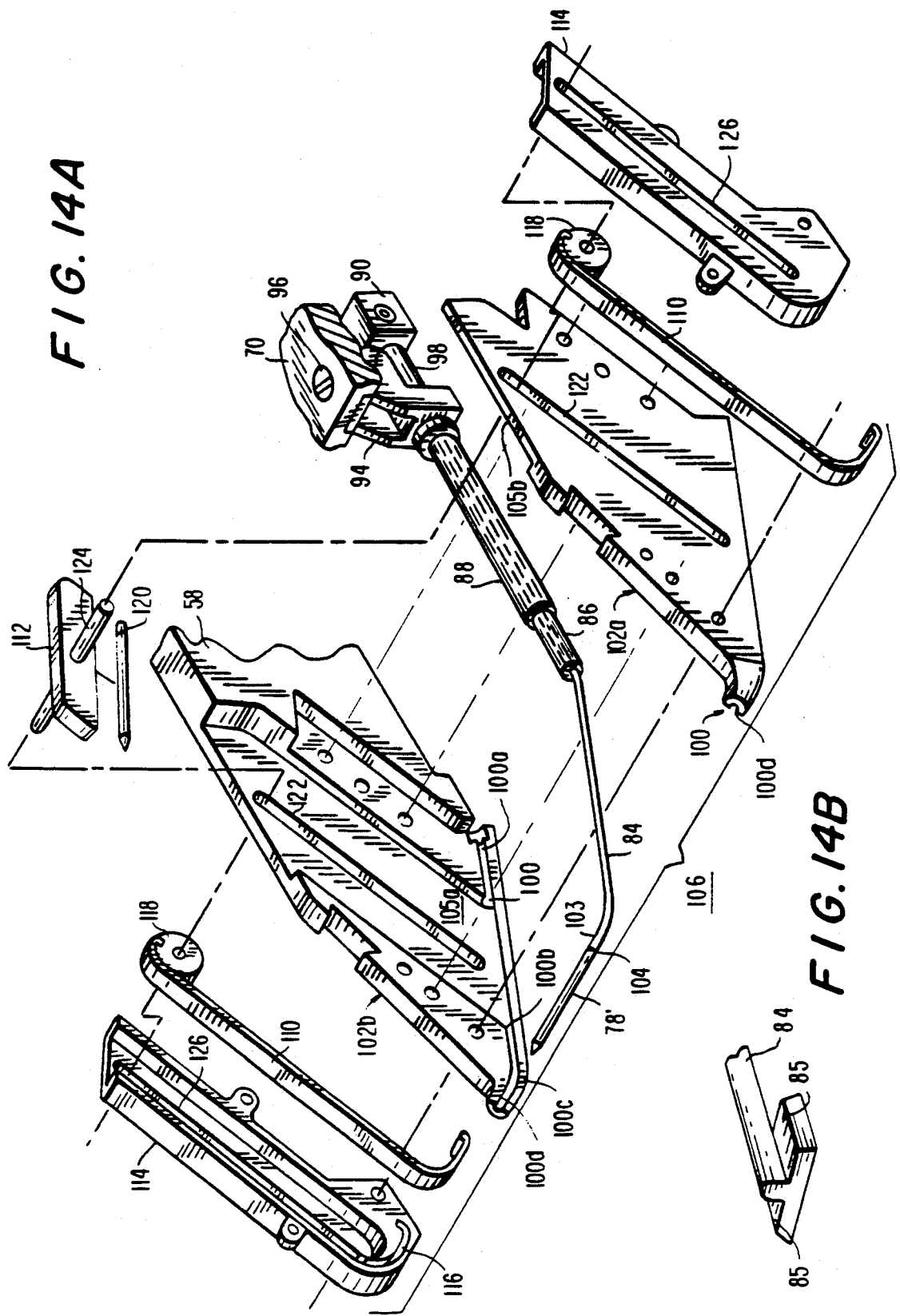

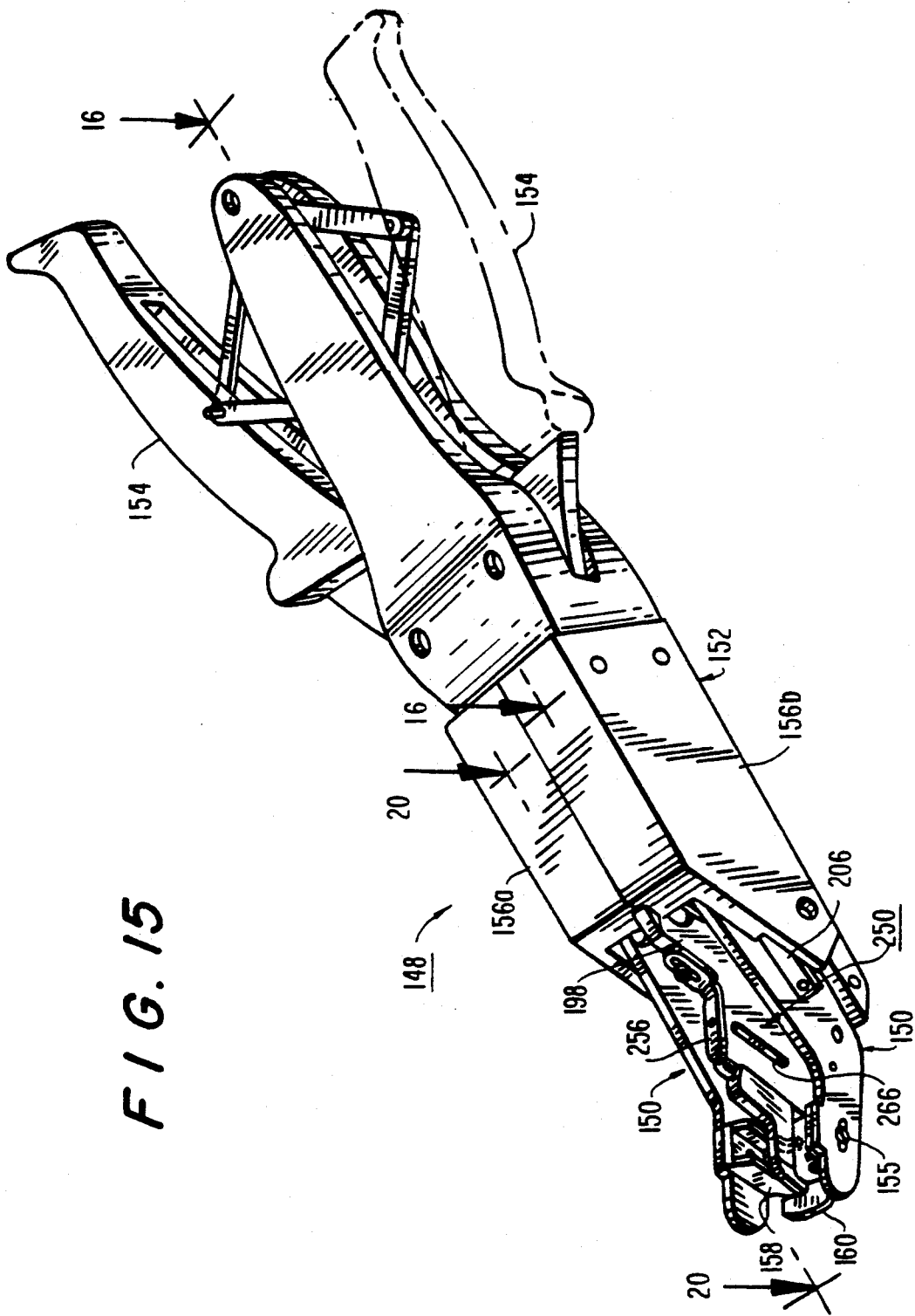

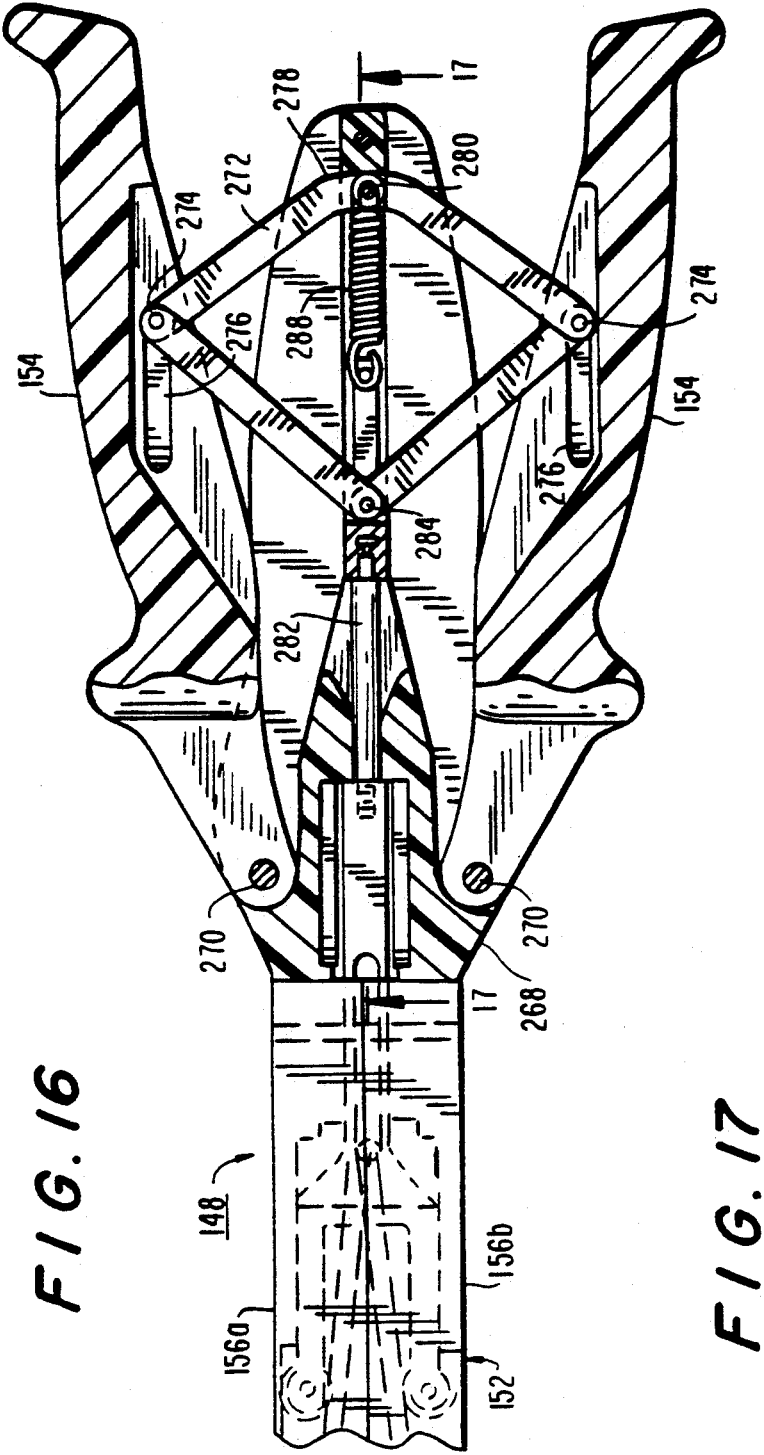

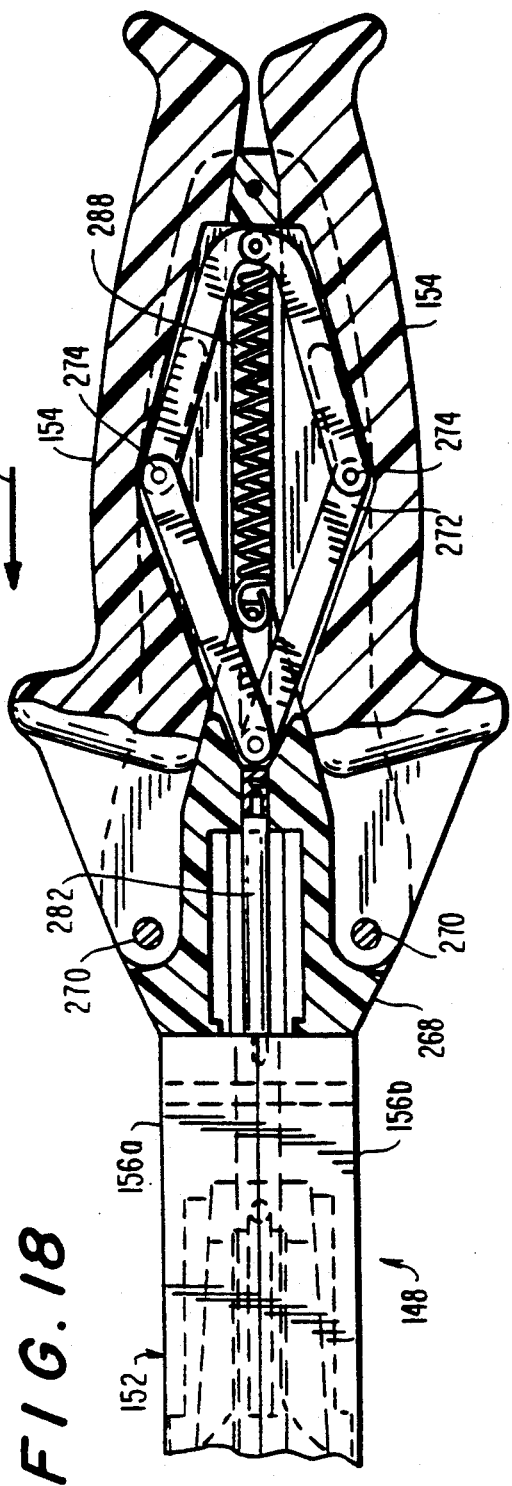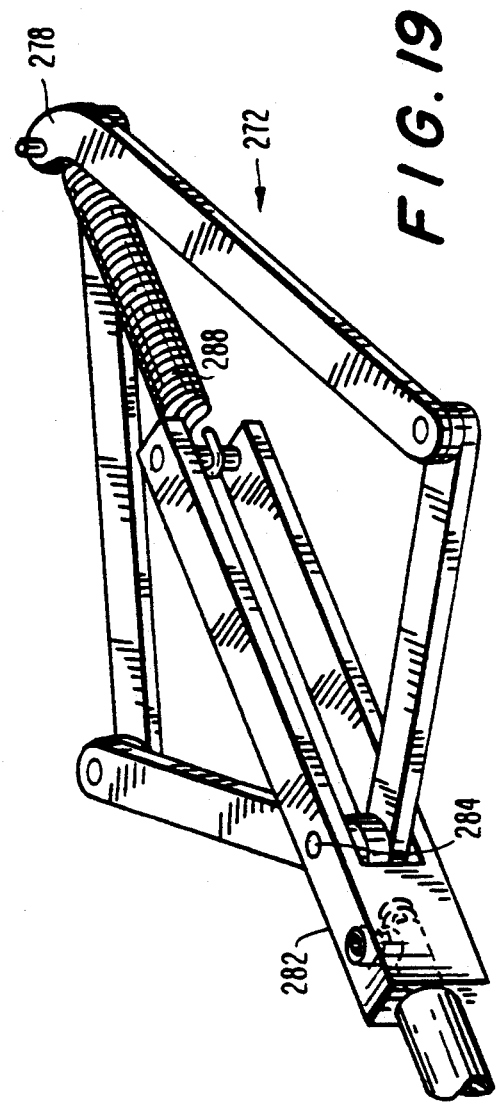

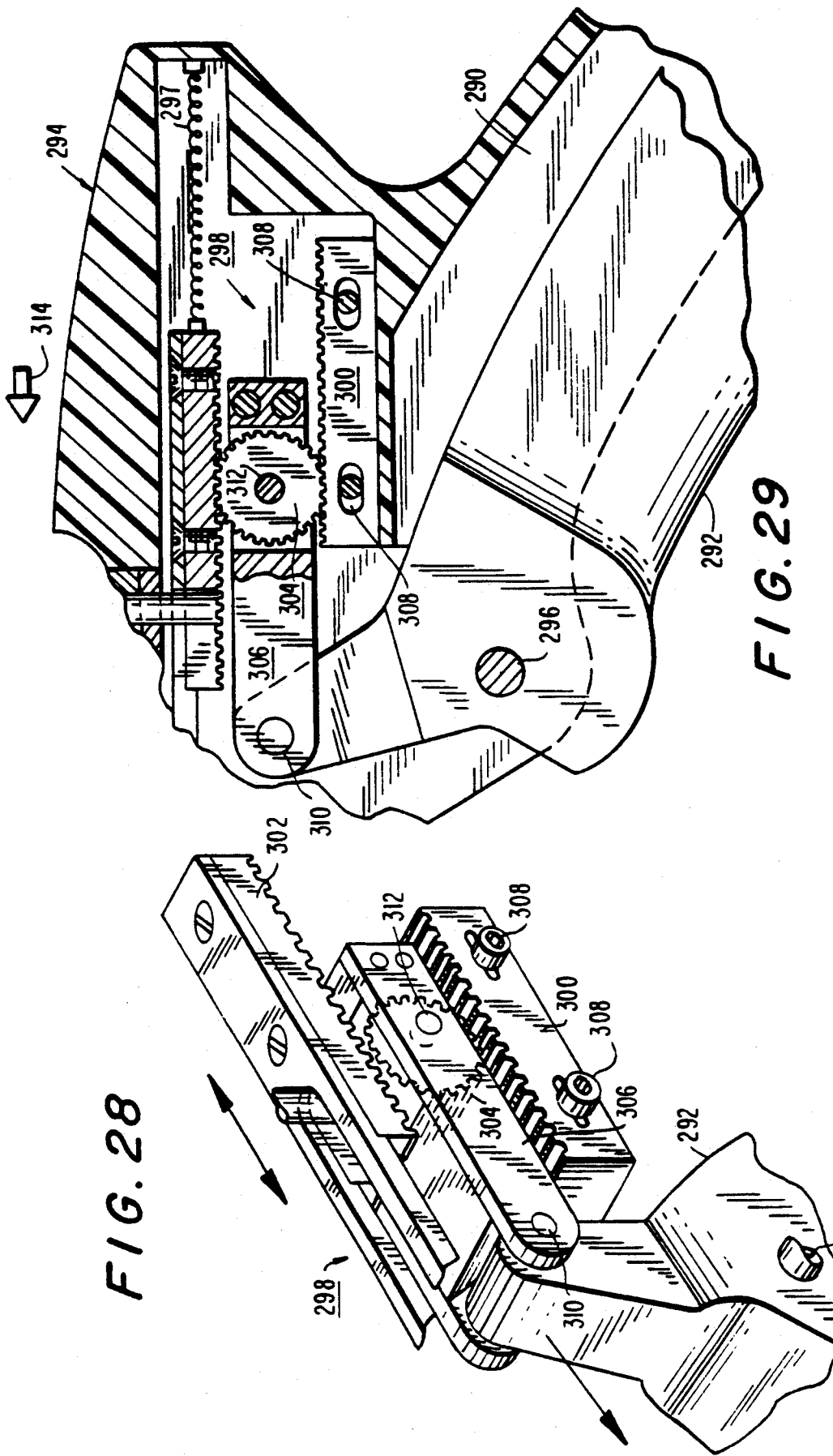

APPARATUS AND METHOD FOR SUBCUTICULAR STAPLING OF BODY TISSUE

CROSS REFERENCE TO RELATED APPLICATION

This application is a continuation-in-part of co-pending applications U.S. Ser. No. 581,776, filed on Sep. 13, 1990, and U.S. Ser. No. 630,224, filed on Dec. 19, 1990.

BACKGROUND OF THE INVENTION

1. Field of the Invention

The present invention relates to an apparatus and method for subcuticular attachment of skin surrounding an opening wherein the opening is either caused unintentionally or by surgical procedure.

2. Discussion Of The Prior Art

Modern day surgery using sutures and staples or the like is well defined. Generally, the key to successfully attaching cutaneous matter is the utmost gentleness in handling all tissue. Damaged and injured tissue leads to necrosis followed by fibrosis and scarring.

In handling tissue for attaching the surgical ends adjacent an opening, care must be taken in attaching the open ends to provide a minimum of the usual well-known telltale marks in the skin. For example, the application of sutures in cutaneous surgery will often result in the appearance of telltale crosshatch markings, whereas the use of sutures subcutaneously allows for early removal to minimize the telltale marks. Application of subcutaneous sutures generally refers to introduction of sutures at well below the epidermis and dermis. Subcuticular sutures generally refer to sutures introduced beneath the epidermis. In any event, reference to attachment of cutaneous matter below the epidermis at any level is sometimes referred to as "subcutaneous."

Surgically attaching cutaneous matter is also accomplished by application of staples which are generally of a metal material and are closed by action against an anvil which causes the ends of the staple to close after piercing the skin surrounding an opening. In either case, the portions of skin are first drawn together and then stapled or sutured so as to hold them together until natural healing takes place. The steps are often cumbersome to the surgeon since holding the skin together requires one motion and stapling or suturing requires another.

To date, there does not appear to exist an apparatus which is capable of gripping the portions of cutaneous matter surrounding an opening and drawing them together, followed by introduction of a staple at subcuticular levels, i.e. below the epidermis. Neither does there appear to exist an apparatus which is capable of drawing the cutaneous matter together and firing a staple in the subcutaneous region, i.e. in the region below the dermis. The present invention is directed to such an apparatus and method for attachment of cutaneous matter.

SUMMARY OF THE INVENTION

A surgical apparatus for attaching at least two adjacent end portions of a medium such as cutaneous body tissue which comprises a pair of jaws carried by a frame, means for moving the jaws toward and away from each other, and body tissue engaging means extending from each jaw and facing the opposed jaw and adapted to engage the respective opposed portions of the medium such that when the jaws are moved from a first open position toward each other to a second closed position, said engaging means causes the two end portions of the medium to be displaced toward each other, drawn together in close approximation, and to assume an irregular or undulating waveform shape whereby an elongated rod-like fastener may be directed generally medially of the medium to attach opposed portions of the medium.

Mechanical means is provided for moving the jaws toward and away from each other by actuation by manually gripping means manually movable toward each other to actuate the mechanical means.

Preferably, the means for moving the jaws toward and away from each other include a cam face on each of the jaws, and cam engaging means provided in the form of a fork that engages against the cam faces to move the jaws toward each other. The fork is slidably carried by the frame, with its tines positioned adjacent the cam faces, and is movable from a first position to a second position to engage its tines against the cam faces and move the opposed jaws towards each other to their closed position.

Included with the means for moving the jaws toward and away from each other is a pair of handles which, when squeezed toward each other, move the fork from its first position to its second position. As the handles are squeezed together, the pivotal motion of the handles is translated to longitudinal motion to move the fork from its first position to its second position.

Plunger means in the form of a plunger rod is provided which is movable from a first position to a second position to engage the elongated rod-like fastener to direct it generally medially of the interface and subcuticularly of the body tissue to thereby attach the end portions. The plunger rod is movable by movement of the fork as it moves from its second position to a third position as the handles are subsequently squeezed further together; the additional pivotal motion of the handles being translated to longitudinal motion to move the fork. When the handles are released, spring action returns the handles, fork and opposed jaws to their first position.

Preferably, each jaw includes a sharp pointed member positioned for engagement with marginal end portions of skin adjacent an opening therein such that when the jaws are displaced toward each other, the skin portions move toward each other and into engagement and assume an undulating waveform configuration at the interface therebetween. The apparatus further comprises a cartridge positioned adjacent the jaws and adapted to support a plurality of elongated rod-like fasteners, each having a sharp pointed tip at its proximal end to facilitate subcuticular penetration of the skin.

Each of the embodiments of the cartridge of the invention include means to resiliently bias the rod-like fasteners toward a position in which the fasteners can be advanced toward the body tissue when the body tissue is gripped by the sharp pointed members.

BRIEF DESCRIPTION OF THE DRAWINGS

Preferred embodiments of the invention are described hereinbelow wherein:

FIG. 1 is a left side perspective view from above, illustrating the improved apparatus for subcuticular fastening of body tissue;

FIG. 2 is a partial cross-sectional view taken along lines 2—2 of FIG. 1;

FIG. 3 is a cross-sectional view with portions cut away, taken along lines 3—3 of FIG. 2;

FIG. 4 is a cross-sectional view taken along lines 4—4 of FIG. 3;

FIG. 5 is a cross-sectional view taken along lines 5—5 of FIG. 3;

FIG. 6 is a greatly enlarged perspective view, of the cam and roller system for moving the pincer jaws of the apparatus toward and away from each other;

FIG. 8 is a perspective view from above, of the pincer jaws of the apparatus in the closed position about an opening in body tissue;

FIG. 9 is a cross-sectional view from above, of the jaw closing mechanism of the apparatus of FIG. 1;

FIG. 10 is a cross-sectional view taken along lines 10—10 of FIG. 9, illustrating a low profile system for storing a plurality of rod-like fastener members;

FIG. 11 is a view taken along lines 11—11 of FIG. 10, illustrating a rod-like fastening member positioned in body tissue to retain the tissue portions on each side of the opening in abutting relation;

FIG. 12 is a frontal view of the pincer jaws of the apparatus of FIG. 10 and the fastening member taken along lines 12—12 of FIG. 11;

FIG. 13 is a cross-sectional view of body tissue portions held by a subcutaneously positioned rod-like fastener member in adjacent engaged relation so as to promote healing;

FIG. 14A is a greatly enlarged perspective view with parts separated for convenience of illustration, showing the portion of the apparatus used for stacking and advancing rod-like fastener members for piercing body tissue;

FIG. 14B is a greatly enlarged perspective view of an alternate embodiment of the mechanism for advancing the fastener members;

FIG. 15 is a perspective view from above illustrating an alternative embodiment utilizing a scissor-type handle for actuating the pincer jaws and the fastener firing mechanism;

FIG. 16 is a partial cross-sectional view of the proximal handle portion of the apparatus of FIG. 15 taken along lines 16—16 of that FIG.;

FIG. 17 is a cross-sectional view taken along lines 17—17 of FIG. 16 illustrating the scissor-type actuating mechanism for closing the jaws and for advancing fastener members;

FIG. 18 is a view similar to FIG. 15 illustrating the manually operable handles in the closed position after firing the fastener member;

FIG. 19 is a greatly enlarged perspective view of the jaw closing and fastener advancing mechanism which forms part of the embodiment of FIG. 15;

FIG. 28 is a perspective view greatly enlarged, of the rack and pinion mechanism of the apparatus shown in FIG. 26; and FIG. 29 is a partial cross-sectional view of the rack and pinion section of the apparatus of FIG. 26 with the rack and pinion system in position corresponding to closed jaws after the fastener has been fired.

DETAILED DESCRIPTION OF THE PREFERRED EMBODIMENTS

Figure 7:
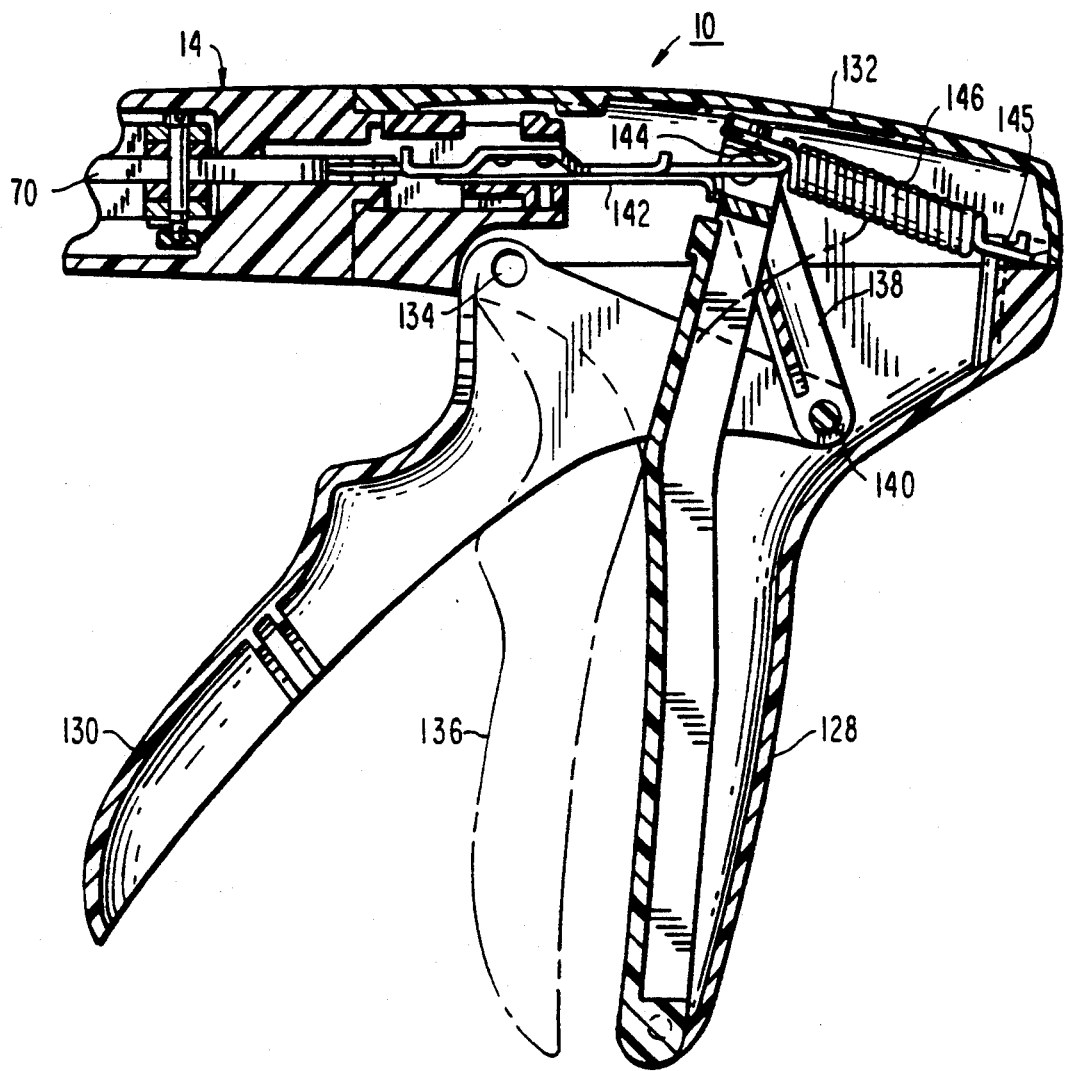
FIG. 7 is a cross-sectional view taken along lines 7—7 of FIG. 1, illustrating the proximal portion of one embodiment of the jaw closing mechanism.

Referring initially to FIG. 1 there is illustrated generally an apparatus 10 for subcuticular stapling of skin constructed according to the present invention. In general, the apparatus includes a pair of opposed jaws 12 movable from a spaced apart open position to a closed position to approximate tissue, a mechanism for camming the jaws to their closed position, and a mechanism for firing fasteners subcuticularly into the approximated tissue portions. A pair of handles 16, extending generally transversely from housing 14, operate to cam jaws 12 and to fire the fasteners in a manner which will be described below.

Jaws 12, which extend from housing 14, are resiliently biased away from each other, and are movable between a normally open position as shown in FIG. 2 to a closed position as shown in FIG. 9. A guide shaft 13 extends slidably through the pair of opposed bores in jaws 12 to provide for accurate alignment of jaws 12 as they are moved between their open and closed positions.

Each jaw 12 includes a transverse gripping member 18 at its free end which is oriented generally at an obtuse angle with respect to its main portion. Transverse gripping members 18 are positioned opposite each other and extend generally toward one another, so that when jaws 12 are moved to their closed position, two portions of partially overlapping body tissue positioned between the gripping members 18 may be advanced into close approximation with each other.

Referring to FIG. 11, one gripping member 18a includes a U-shaped member 30 having a pair of spaced, sharp pointed skin gripping tips 28 with serrated ends which extend generally toward the opposite gripping member 18. U-shaped member 30 is removably attached to arm 24a by suitable means such as a screw 32. One end of the base of U-shaped member 30 may include a locator pin 34 positioned in a notch 36 in arm 24a to aid in restraining U-shaped member 30 from turning about screw 32.

The opposite gripping member 18b includes a pair of closely spaced, sharp pointed skin gripping tips 38 that are positioned medially between tips 28. As shown in FIG. 11, skin gripping tips 38 may similarly be provided in the form of a U-shaped member 40 having serrated tips at the ends of its closely spaced prongs, and removably attached to arm 24b by suitable means such as a screw 42. The base 44 of U-shaped member 40 may extend outwardly from prongs 46, laterally along arm 24b. One end of base 44 may include a locator pin 48 which is positioned in a notch 50 in arm 24b and aids in restraining U-shaped member 40 from twisting about screw 42.

Gripping member 18b may also include a third serrated skin gripping tip 52 in the form of an angularly oriented prong 54. Prong 54 is spaced from prongs 46 and is positioned so that its serrated skin gripping tip 52 is located outside tips 28. When jaws 12 are brought together as described in detail below, tips 28, 38, and 52 grip the portions of skin surrounding a body opening in a partially overlapping, sinusoidal waveform configuration as indicated by phantom line 56. Clearly, other configurations of prongs or a different number of prongs can be utilized to perform the function of approximating and holding the skin.

Referring to FIG. 2, housing 14 provides a frame for carrying jaws 12 and includes housing halves 19a, 19b, and removable cover 17 to allow ready access to the interior for ease of assembly. Elongated hollow 22 extends longitudinally into the end of housing 14 opposite handles 16. Each jaw 12 includes an elongated arm 24 extending generally longitudinally from hollow 22 with its transverse gripping members 18 positioned outside of housing 14. Arms 24 are pivotally interconnected inside the housing by a pin 26 for movement toward and away from each other and are of sufficient structural rigidity to retain their shape when jaws 12 are moved to their closed positions. Alternatively, jaws 12 and arms 24 may be formed integrally, interconnected at their enclosed ends by a transverse web.

With continued reference to FIG. 2, a longitudinal divider is positioned between arms 24 and connected thereto at its enclosed end by pin 26. Divider 58 bisects hollow 22 and extends outwardly from hollow 22, terminating at front stabilizer plate 20. A pair of arcuate leaf springs 60 are positioned symmetrically about divider 58. The innermost ends of springs 60 are attached to divider 58 by suitable means such as a rivet 62, shown in FIGS. 3 and 10. Leaf springs 60 bias outwardly so that their free ends bias against arms 24 of jaws 12 to normally urge jaws 12 to their open position. A longitudinal slot 64, shown in phantom, extends along each side of divider 58 to provide a recess into which leaf springs 60 may longitudinally recede as jaws 12 are moved to their closed position, as shown in FIG. 9.

As best shown in FIG. 3, the foot of housing 14 provides a rear stabilizer portion 21. Front stabilizer 20 and rear stabilizer 21 assist in stabilizing the position of the apparatus 10 during attachment of portions of body tissue as hereinafter described. Alignment pin 59, which may be retractable, extends downwardly from front stabilizer plate 20.

Referring now to FIG. 6, the mechanism for closing the jaws 12 will be described. Each arm 24 of jaw 12 includes a cam section 66 having a cam face 68 positioned at an acute angle to arm 24. Each cam section 66 can be formed of stainless steel or other suitable materials. Accordingly, preferably cam section 66 is provided in the form of an insert which is molded to arm 24. Alternately, cam section 66 and cam face 68 may be formed integrally with arms 24.

Fork 70, as shown in FIGS. 2 and 6, is carried by housing 14 and is adapted to come into contact with cam faces 68 to close the jaws. Fork 70 is longitudinally mounted in housing 14 within a slot provided in divider 58 (not shown in the FIGS.). Referring to FIG. 3, fork 70 includes a longitudinal slot 71 through which pin 26 extends. Fork 70 is located in hollow 22 with the ends of its tines 72 having rollers 74 which roll along cam faces 68 as best shown in FIG. 6. As an alternate to rollers 74, a flatter surface to frictionally engage cam faces 68 can be provided. As shown in FIGS. 2 and 9, rollers 74 contact opposed inner wall portions 76 defining hollow 22 during the longitudinal movement of fork 70 from a proximal (first) position, as best seen in FIGS. 2 and 3, to a distal (third) position, shown in FIGS. 9 and 10. During this movement, fork 70 assumes an intermediate (second) position in which rollers 74 engage against cam faces 68, moving arms 24 toward each other and biasing springs 60 laterally into slots 64, to move jaws 12 to their closed position, as shown in FIG. 9.

Referring to FIG. 10, further longitudinal movement of fork 70 to its distal position causes a flexible, elongated rod-like fastener 78 to be ejected into a path between closed jaws 12. Fastener 78 has a sharp penetration tip 79 at its forward or proximal end (see FIGS. 11 and 13) and is described in parent applications U.S. Ser. No. 581,776, filed on Sep. 13, 1990, and U.S. Ser. No. 630,224, filed on Dec. 19, 1990. Each of the fasteners 78 are of length sufficient to engage oppositely sloped skin portions as determined by the dimensions and relative spacing of the pointed tips. Each of the fasteners 58 may include means on the outer surface for improved retention in position within the body tissue.

Referring now to FIG. 12, each transverse gripping member 18a, 18b includes a notch 80 which is alignable with the opposing notch 80 when jaws 12 are moved to their closed position. As can be appreciated, notches 80 provide a longitudinal void 82 which is coincidental with the path of the fastener 78.

Turning now to the mechanism for firing the fasteners through longitudinal void 82 and into the approximated body tissue sections, ejection mechanism 83 shown generally in FIGS. 3, 10 and 14 is positioned adjacent jaws 12 and includes an elongated plunger 84, an inner elongated stationary tubular member 86, and an outer tubular member 88, which concentrically surrounds tubular member 86 and is adapted to move longitudinally therealong. Stationary tubular member 86 is secured within a bore 89 adjacent the lower end portion of divider 58 by a screw 91, and extends longitudinally into the lower portion of hollow 22. Referring to FIG. 14, elongated plunger 84 comprises a flexible wire-like rod that extends longitudinally through stationary tubular member 86 and into tubular member 88 where it is secured at its proximal end by suitable means so that it moves longitudinally with tubular member 88. Plunger 84 is preferably made of a super elastic metal. One example of such metal is NITINOL brand metal available from Raychem Corporation, Menlo Park, Calif. Clearly, other resilient materials can be utilized. As will be appreciated in the illustrated embodiment, the cross-section of plunger 84, at least at its distal end, is approximately equal to the cross-section of rod-like fastener 78.

Outer tubular member 88 and connected plunger 84 is movable longitudinally between a proximal (retracted) position as shown in FIG. 3 coinciding with the proximal position of fork 70, and a distal position as shown in FIG. 10, coinciding with the distal position of fork 70 to discharge fastener 78. Alternatively, as shown in FIG. 14B, the plunger 84 can include a transverse tab 85 which rides in a channel formed by the two cartridge halves to restrain movement of the plunger 84. The tab may optionally be positioned at a central portion of the plunger 84.

Referring again to FIGS. 3 and 10, stop block 90 is secured at the free end of outer tubular member 88. Annular abutment 92 surrounds outer tubular member 88 and is located distally of stop block 90. Crosshead guide 94 extends laterally from fork 70, and is connected thereto by screw 96 shown in FIG. 14 such that it moves with fork 70. Crosshead guide 94 is provided with a bore in which outer tubular member 88 is slidably positioned and is located between stop block 90 and annular abutment 92. Crosshead guide 94 is longitudinally movable along tubular member 88 from a position which contacts stop block 90, coinciding with the proximal position of fork 70, to a position which abuts annular abutment 92, coinciding generally adjacent the conclusion of the movement of fork 70 to the intermediate position (compare FIGS. 3 and 10). Thus, outer tubular member 88 moves with fork 70 as it moves to its distal position. During the return movement of fork 70 to its proximal position, tubular member 88 and fork 70 move together to return plunger 84 to the proximal position until crosshead guide 94 abuts stop block 90.

As best shown in FIGS. 3 and 10, plunger 84 travels along non-linear path 100 which is defined by linear segments 100a, 100b and arcuate segment 100c terminating in a linear segment 100d. Segment 100d is axially aligned with longitudinal void 82. As shown in FIG. 14, path 100 is formed by cartridge body halves 102a, 102b. As will be appreciated, path 100 provides a means for altering the directional vector of the ejected rod-like fastener 78.

Referring now to FIGS. 3, 4 and 14, the cartridge for storing the fasteners will be described. Fastener cartridge 106 shown in FIG. 3 is adapted to retain a number of rod-like fasteners 78 for sequential ejection, one at a time, in end to end relationship to fasten the end portions of body tissue in an opening which is greater in length than the length of a single fastener 108. Fastener cartridge 106 is configured to allow diagonal stacking of the fasteners to reduce the profile of the distal portion of the apparatus to increase the visibility of the user during operative procedures. This diagonal stacking also increases the number of fasteners which can be stored in the apparatus. The cartridge may optionally be removably mounted in the apparatus to allow removal and replacement with another loaded cartridge.

The casing of fastener cartridge 106 includes body halves 102a, 102b which are attached together by suitable means. As shown, body half 102b may be formed integrally with divider 58, extending forwardly at the front end therefrom toward transverse gripping members 18.

Each body half 102a, 102b includes an elongated chamber portion 105a, 105b which cooperate when body halves 102a, 102b are assembled together to provide a chamber 105 in which fasteners 108 are stacked laterally in face-to-face contacting relationship along their respective longitudinal surfaces. The cross-sectional dimension of chamber 105 is equal to or slightly greater than the major diameter of each rod-like fastener 108 to facilitate a snug fit, with the angular longitudinal length of chamber 105 being dimensioned to accommodate a predetermined number of fasteners 108. Chamber 105 extends rearwardly at an acute angle, thus allowing fasteners 108 to be stacked in diagonal fashion, in a cascading, partially overlapping lateral arrangement which ascends rearwardly as shown. This arrangement advantageously conserves space as compared to vertical stacking.

As shown in FIG. 4, fasteners 108 are biased downwardly in chamber 105 toward the firing chamber segment which extends between segments 100a, 100b. The bottommost fastener 78 is biased into the firing chamber segment where it is retained for ejection as its distal end 104 is adjacent operative end 103 of plunger 84. After each fastener 78 is ejected and discharged, plunger 84 is withdrawn longitudinally to its retracted position with the end 103 of plunger 84 returning to segment 100a, to allow the next fastener 78 to be biased downwardly into the firing chamber segment into a position suitable for egress from the fastener stack.

More particularly, as shown in FIG. 14, a pair of negator springs 110 act on transverse shaft 124 of follower 112 to bias fasteners 78 downwardly. Each negator spring 110 is positioned within a jacket 114 as shown, with its lower end secured within an arcuate slot 116 formed therein and its other end secured to a circular bushing 118. Each negator spring 110 in its initial position is partially unwound, the spring being resiliently biased toward a normal spiral configuration. As follower 112 slides downwardly in the chamber 105, the spring winds towards its spiral configuration. Follower 112 is positioned in chamber 105 adjacent the topmost member 120 of the stacked rod-like fasteners 78. Furthermore, a longitudinal slot 122 bisects each chamber portion 105a, 105b as shown and receives and holds one end of transverse shaft 124 of follower 112 as it moves downwardly in chamber 105 towards the firing chamber segment. The ends of shaft 124 are also held within the bore portions of bushings 118. Each jacket 114 may be provided with an elongated window 126 through which the position of follower shaft 124 may be visually observed to indicate the remaining number of rod-like fasteners 108 which are available.

Referring now to FIG. 7, a preferred mechanism for closing the jaws and for actuating plunger 84 is illustrated and includes handles 128, 130 extending generally transversely from housing portion 132. Handle 128 is formed integrally with housing portion 132 and handle 130 is pivotally connected via pin 134 to housing portion 132 for movement between an open position and closed position, as indicated by phantom lines 136 in FIG. 7. Squeezing of handle 130 toward handle 128 moves fork 70 from its proximal position to its distal position to thereby close jaws 12 and move plunger 84 longitudinally to discharge fastener 78 as will be described in more detail below.

A link member 138, pivotally connected via pin 140 to handle 130, translates the pivotal motion of handle 130 to longitudinal motion which moves fork 70 longitudinally distally. More specifically, link member 138 is pivotally connected via pin 144 to the rear end of drawbar 142, and drawbar 142 is connected at its distal end to the proximal end of fork 70. A spring 146 is attached to the proximal end of drawbar 142 and to housing portion 132, to cause drawbar 142 to move proximally when handles 128, 130 are released, thus returning fork 70 to its proximal position. Movement of drawbar 142 rearwardly also returns handles 128, 130 to their open position.

In operation, handles 130, 128 are initially squeezed together to move fork 70 distally such that rollers 74 engage cam faces 68 to force the jaws toward each other to bring the tissue portion into overlapping relationship and into an undulating configuration. Further squeezing of handles 128, 130 causes plunger 84 to move from its retracted position toward its discharge position so that its operative end 103 engages the lowermost fastener 78, positioned between segments 100a, 100b, causing it to be ejected (i.e. fired) distally into segment 100b. Continued movement of plunger 84 by fork 70 causes fastener 78 to move forwardly through arcuate segment 100c and to segment 100d where fastener 78 is discharged to penetrate the end portions of body tissue to attach the and portions together.

FIG. 15 illustrates generally another embodiment of the apparatus of the present invention, having a scissor-type handle mechanism. Apparatus 148 includes a pair of opposed jaws 150, similar to opposed jaws 12 in FIG. 1, extending from the distal end of housing 152 which encloses the jaw closing mechanism. A pair of handles 154 extend generally proximally from the proximal end of housing 152. Jaws 150 are resiliently biased away from each other, and are movable from their normally open position toward each other to a second closed position by squeezing handles 154 together. A guide shaft 155 similar to guide shaft 13 of FIG. 1 extends slidably through a pair of opposed bores in jaws 150 to restrain twisting of jaws 150 as jaws 150 are moved between their open and closed positions. Housing 152 may further comprise housing halves 156a, 156b, as shown, for ease of assembly.

Each jaw 150 includes transverse gripping members 158, similar to the transverse gripping members 18 shown in FIG. 1, oriented generally at an appropriate obtuse angle with respect to the main portion of the respective jaw 150. Accordingly, reference is made to the previous description in connection with FIG. 11 in conjunction with the gripping members 158 shown in FIG. 15. When jaws 150 are moved toward each other to a closed position, the two portions of partially overlapping bodily tissue positioned between gripping members 158 are brought into close approximation. Further movement of handles 154 toward each other causes thin elongated rod-like fastener 220, described above, to be discharged between gripping members 158 to penetrate the body tissue portions and attach the two body tissue portions together as described previously.

Figure 21:
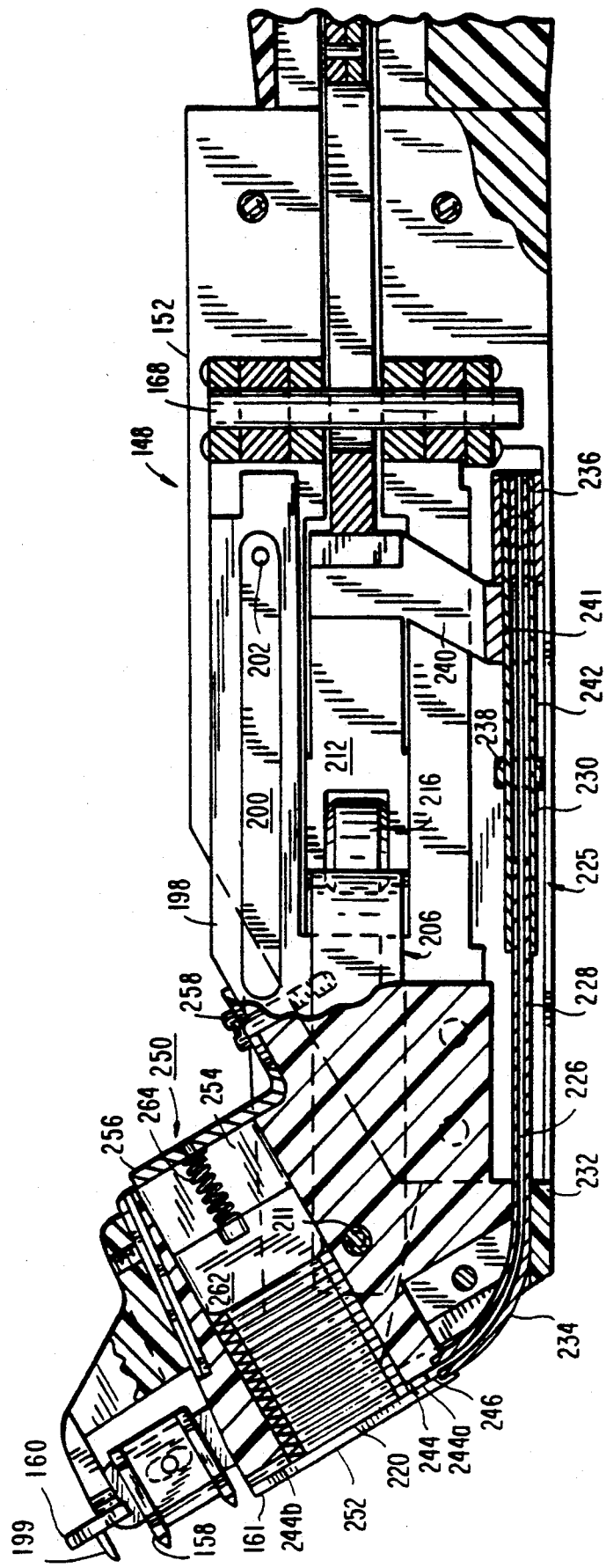
FIG. 21 is a cross-sectional view of the distal section of the apparatus shown in FIG. 15 illustrating an alternative type of fastener storing cartridge.
Figure 25:
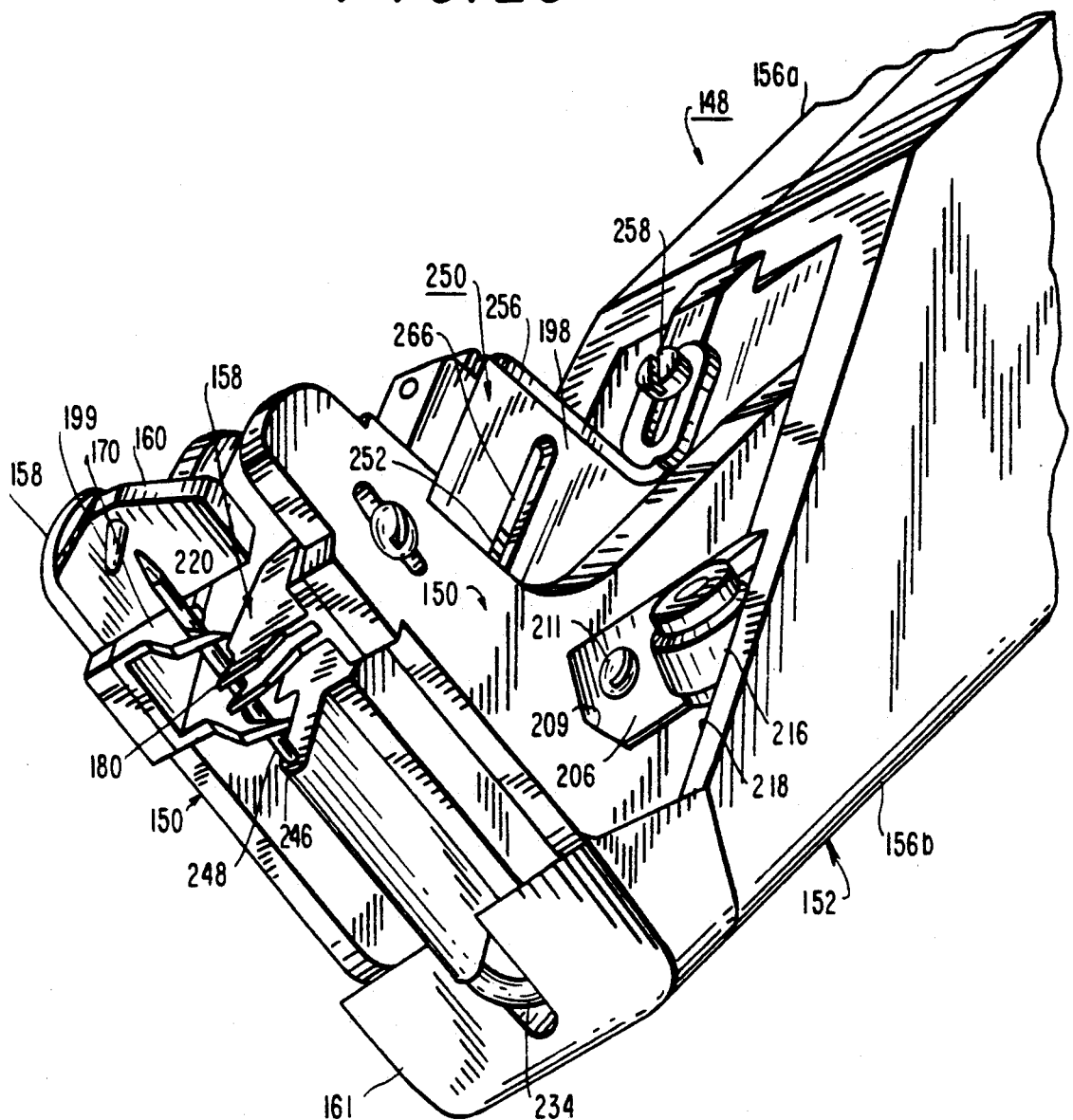
FIG. 25 is a view from below of the pincer jaws of the apparatus of FIG. 15 in the closed position during actuation of the fastener firing mechanism.

Referring to FIGS. 21 and 25, front stabilizer portion 160 includes an alignment pin 199, preferably retractable, extending downwardly therefrom. The foot of housing 152 provides a proximal stabilizer portion 161. Stabilizers 160 and 161 assist in stabilizing apparatus 148 during attachment of portions of body tissue as described below.

Figure 20:
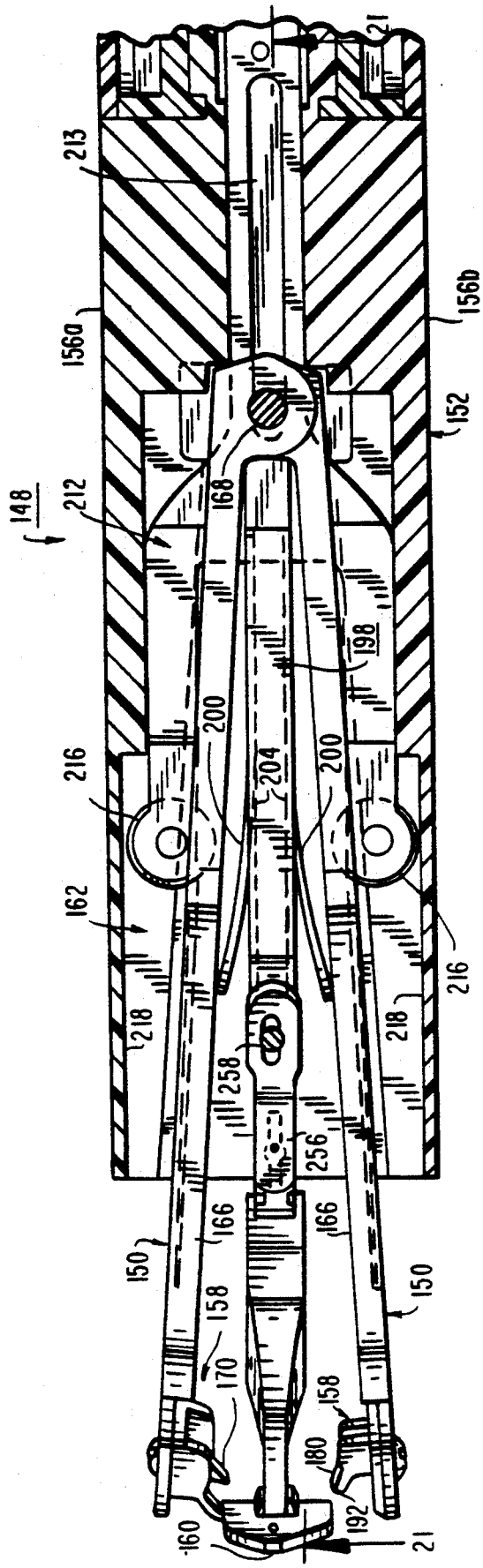
FIG. 20 is a cross-sectional view of the apparatus of FIG. 15 illustrating the roller-cam mechanism for closing and opening the pincer jaws.

Referring to FIG. 20, housing 152 provides a frame for carrying jaws 150. Jaws 150 extend into hollow 162 of housing 152 similar to the previous embodiment. Each jaw 150 includes an elongated arm 166 extending generally longitudinally from hollow 162 with its transverse gripping members 158 positioned outside of housing 152. Arms 166 are pivotally interconnected at their proximal ends by a pin 168 for movement toward and away from each other. Alternately, jaws 150 and arms 166 may be formed integrally, interconnected at their enclosed ends by a transverse web.

As in the first embodiment described above, a longitudinal divider 198 bisects hollow 162 and terminates at stabilizer plate 160. A pair of arcuate leaf springs 200 are attached to divider 198 by a rivet 202, shown in FIGS. 21 and 24, and bias jaws 150 to their open position. Longitudinal slots 204 provide a recess to receive leaf springs 200 when jaws 150 are moved to their closed position, as shown in FIG. 23.

Figure 22:
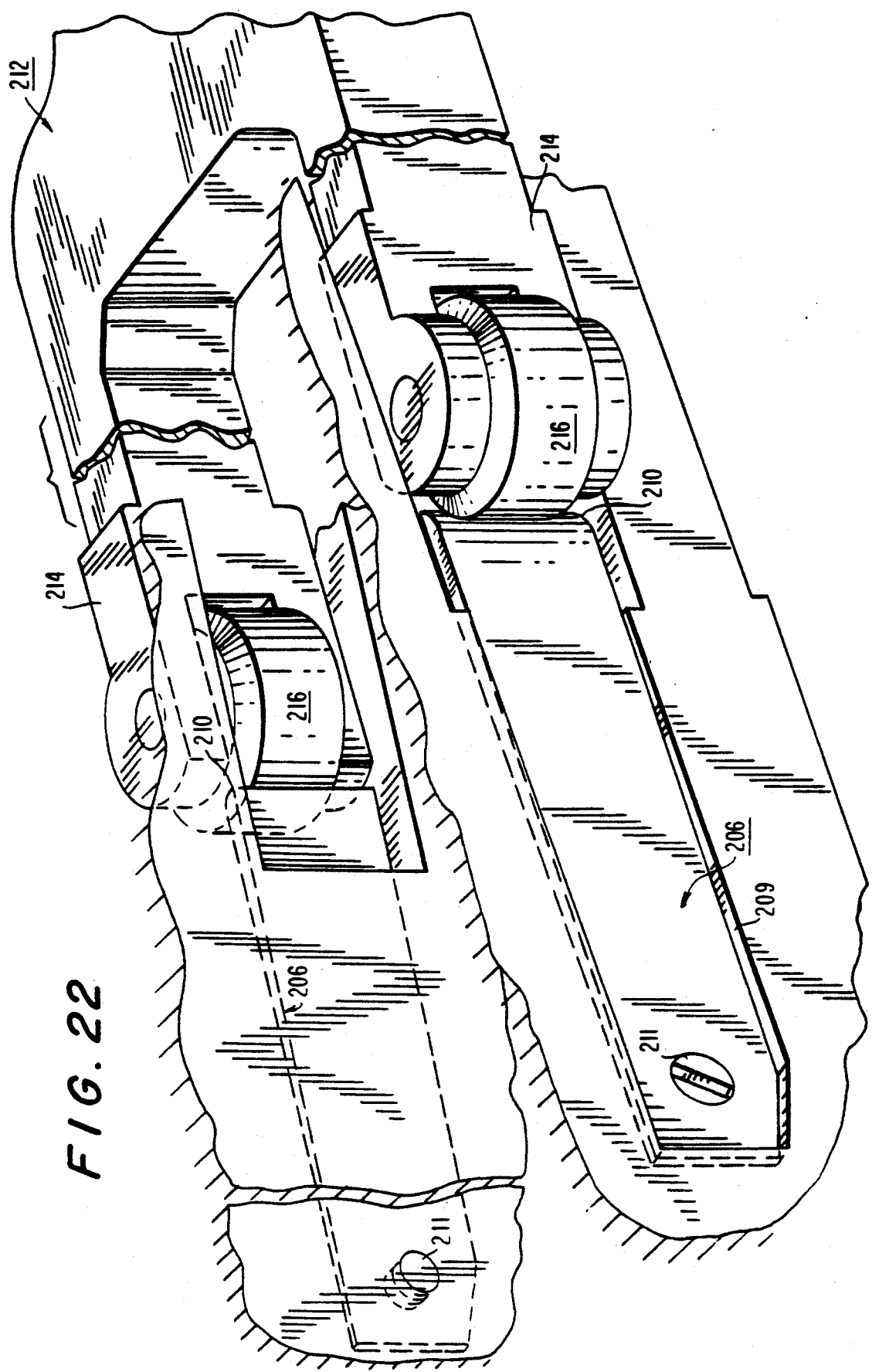
FIG. 22 is a greatly enlarged view from above illustrating the roller cam for closing and opening the pincer jaws of the apparatus of FIG. 15.

Referring to FIG. 22, each arm 166 includes a cam member 206 positioned along its outer face 208 and retained within a slot 209 in arm 166 by screw 211. Each cam member 206 includes a rearward facing beveled edge 210.

Figure 23:
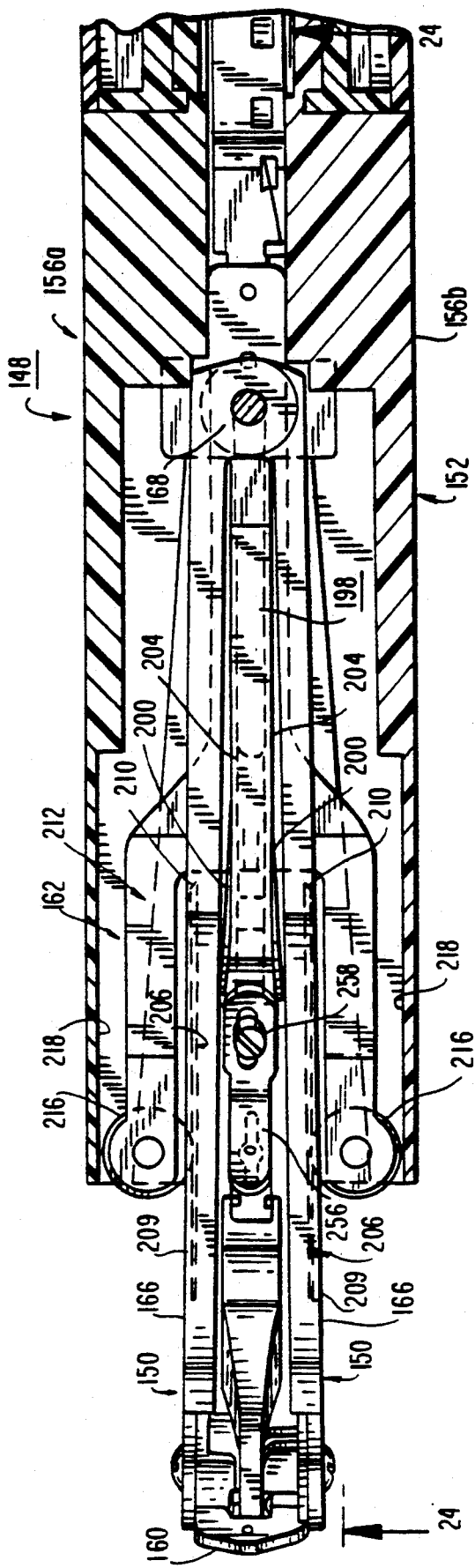
FIG. 23 is a cross-sectional view similar to the view shown in FIG. 20 with the pincer jaws in the closed position.

Fork 212, carried by housing 152, is similar to fork 70 in that it includes a longitudinal slot 213 through which pin 168 extends and has rollers 216 at the end of each tine to roll along and engage cam member 206 when moved from a proximal position, as best seen in FIGS. 20, to a distal position, shown in FIG. 23. Rollers 216 are positioned in elongated slots 218 in the interior wall of housing 152 to prevent twisting of fork 212 within hollow 162. Rollers 216 contact the opposed recessed wall portions of slots 218, and roll along recessed wall portions of slots 218 during the longitudinal movement of fork 212. The movement of fork 212 between its proximal position, intermediate position, and distal position for firing the fastener 220 is identical to the previous embodiment described with reference to FIGS. 2 and 6.

Figure 24:
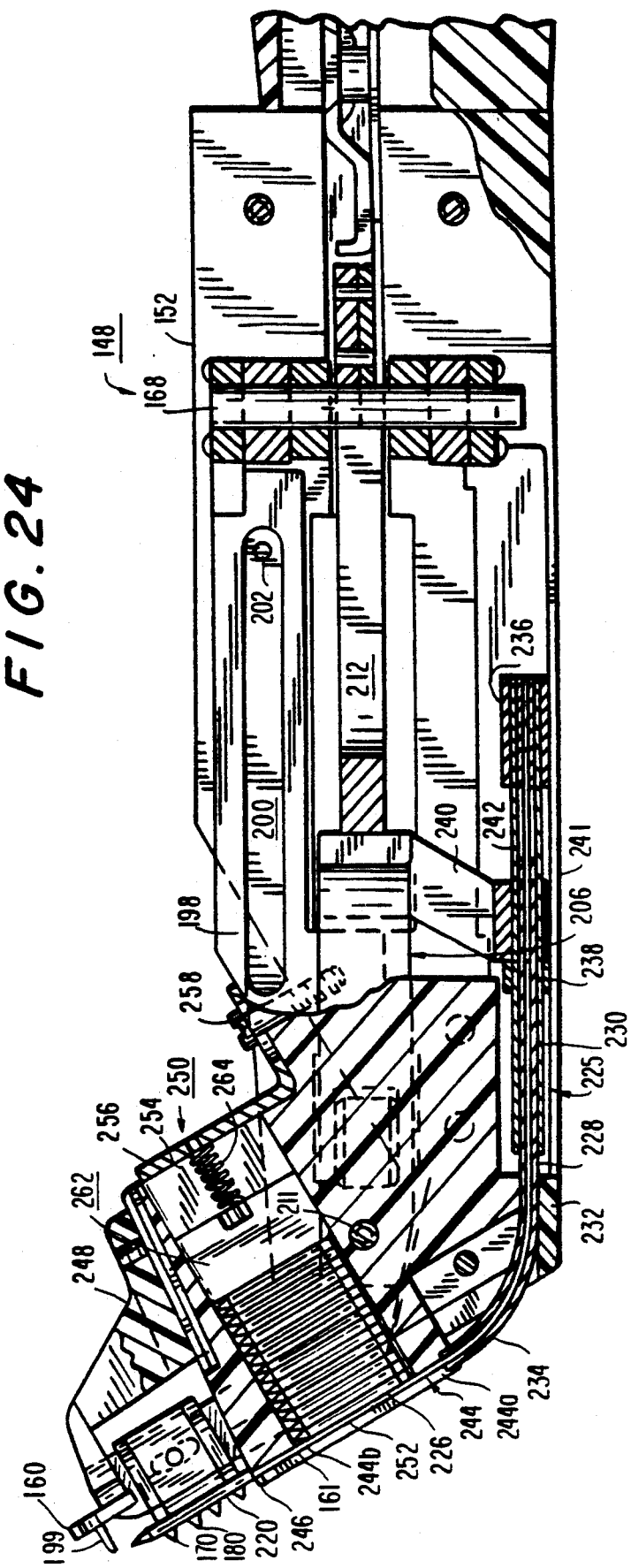
FIG. 24 is a cross-sectional view similar to the view shown in FIG. 21 with the firing mechanism advanced for firing a fastener.

The mechanism 225 (FIG. 21) for ejecting fasteners 220 are similar to that described with respect to the first embodiment. The mechanism includes an elongated plunger 226, an inner, elongated stationary tubular member 228 and a longitudinally movable outer tubular member 230, which concentrically surrounds tubular member 228 and is adapted to move longitudinally therealong. Referring to FIGS. 21 and 24, tubular member 228 is secured within a bore 232 and includes an arcuate, curved portion 234. Plunger 226 comprises a flexible wire-like rod, preferably composed of the same material as plunger 84, that extends longitudinally through stationary tubular member 228 into tubular member 230. As may be appreciated, the cross-section of the wire-like rod approximately matches the cross-section of fastener 220. The enclosed end of plunger 226 is secured within tubular member 230 such that plunger 226 moves longitudinally with tubular member 230.

In operation, the mechanism for approximating the body tissue and for firing the rod-like fasteners is identical to the operation described for the embodiment shown in FIGS. 2–6. However, the actual rod-like firing system is unique in some respects to the embodiment of FIG. 15 as is described below.

Referring once again to FIG. 21, path 244 comprises a pair of spaced, axially aligned segments 244a, 244b, with segment 244a connecting with arcuate, curved portion 234 of tubular member 228, and segment 244b connecting with longitudinal void 224 formed between the closed jaws. Path 244 is similarly provided by furnishing the cartridge body extension of divider 198, hereinafter described, with bore-like passages constructed as previously described.

Prior to ejection, fastener 220 is axially aligned between segments 244a, 244b and plunger 226 and is positioned in segment 224a with its proximal end 246 abutting the distal end 248 of fastener 220. Upon movement of fork 212 from its intermediate to its distal position, crosshead guide 240 abuts annular abutment 238, allowing outer tubular member 230 and plunger 226 to be moved longitudinally (see FIG. 24) to eject (fire) fastener 220 through segment 244b to penetrate the overlapped end portions of body tissue held between transverse jaw members 158a, 158b. Plunger 226 is subsequently withdrawn to its original position by return of fork 212 to its proximal position.

With continued reference to FIGS. 21 and 24, an alternative fastener cartridge 250 is shown which is adapted to hold a plurality of fasteners 220 for sequential ejection, one at a time in end to end relationship, into body tissue. The body of fastener cartridge 250 is formed of attachable casing halves and is preferably integral with divider 198.

Elongated chamber 254 of cartridge 250 is configured and dimensioned to stack fasteners 220 vertically in face-to-face contacting relationship along their respective longitudinal surfaces. The cross-sectional dimension of chamber 254 is equal to or slightly greater than the major diameter of each rod-like fastener 220 to facilitate a snug fit for each fastener 220 within the chamber.

Fasteners 220 are biased downwardly in chamber 254 by spring 264 and follower 262 (FIGS. 21 and 24), with the lowermost fastener in the segment between bore-like segments 244a, 244b. After each fastener 220 is ejected, plunger 226 is withdrawn longitudinally into segment 244a to allow the next fastener 220 to move into the firing chamber segment as spring 264 exerts a force on follower 262.

Cover 256 is removably fastened to housing 152 by a screw 258. The upper end of spring 264 is retained by a nipple formed on the underside of cover 256, and the lower end of spring 264 is retained in a slot formed in the top portion of follower 262. Removable cover 256 allows access to fasteners 252 and allows the cartridge 250 to be removed and replaced with another loaded cartridge. The new cartridge can optionally contain fasteners of a different size. Elongated window 266 bisects opposite side portions of chamber 254 to allow the position of follower 262 to be visually observed to indicate the remaining number of fasteners 252 (See FIGS. 15 and 25).

Referring to FIGS. 15-19, a pair of handles 154 are shown for moving fork 212 between its proximal and distal positions. Although the handle mechanism is described for use in the embodiment of FIG. 15, it can also be used as an alternative to handles 128 and 130 of the embodiment of FIG. 1 for actuating fork 70. Handles 154 extend generally rearwardly from handle portion 268 and are pivotally connected to handle portion 268 by pivot pins 270 for movement between an open position as shown in FIG. 16, to a closed position as shown in FIG. 18.

Squeezing handles 154 together actuates parallelogram transmission 272 to cause jaws 158 to move to their closed position and plunger 226 to move longitudinally from its retracted position to its extended position to eject and discharge fastener 220. Parallelogram transmission 272 is pivotally connected at opposite ends thereof to handles 154 by pins 274 slidably mounted within elongated slots 276, so that the pivotal motion of handles 154 toward and away from each other allows parallelogram 272 to expand and contract.

Pin 280 connects parallelogram transmission 272 at its proximal end 278 to the handle portion 268 and pin 284 connects transmission 272 at its distal end to drawbar 282. As parallelogram 272 contracts under the influence of the pivotal motion of handles 154, causing its forward end to move longitudinally forward in the direction of arrow 286, longitudinal motion is transferred to drawbar 282 which being connected to fork 212, transfers longitudinal motion thereto. A spring 288 attached between the rear end of drawbar 282 and the handle portion 268 causes drawbar 282 to move rearwardly when handles 154 are released, thus returning fork 212 to its proximal position. Movement of drawbar 282 rearwardly also returns handles 154 to their open position.

Figure 26:
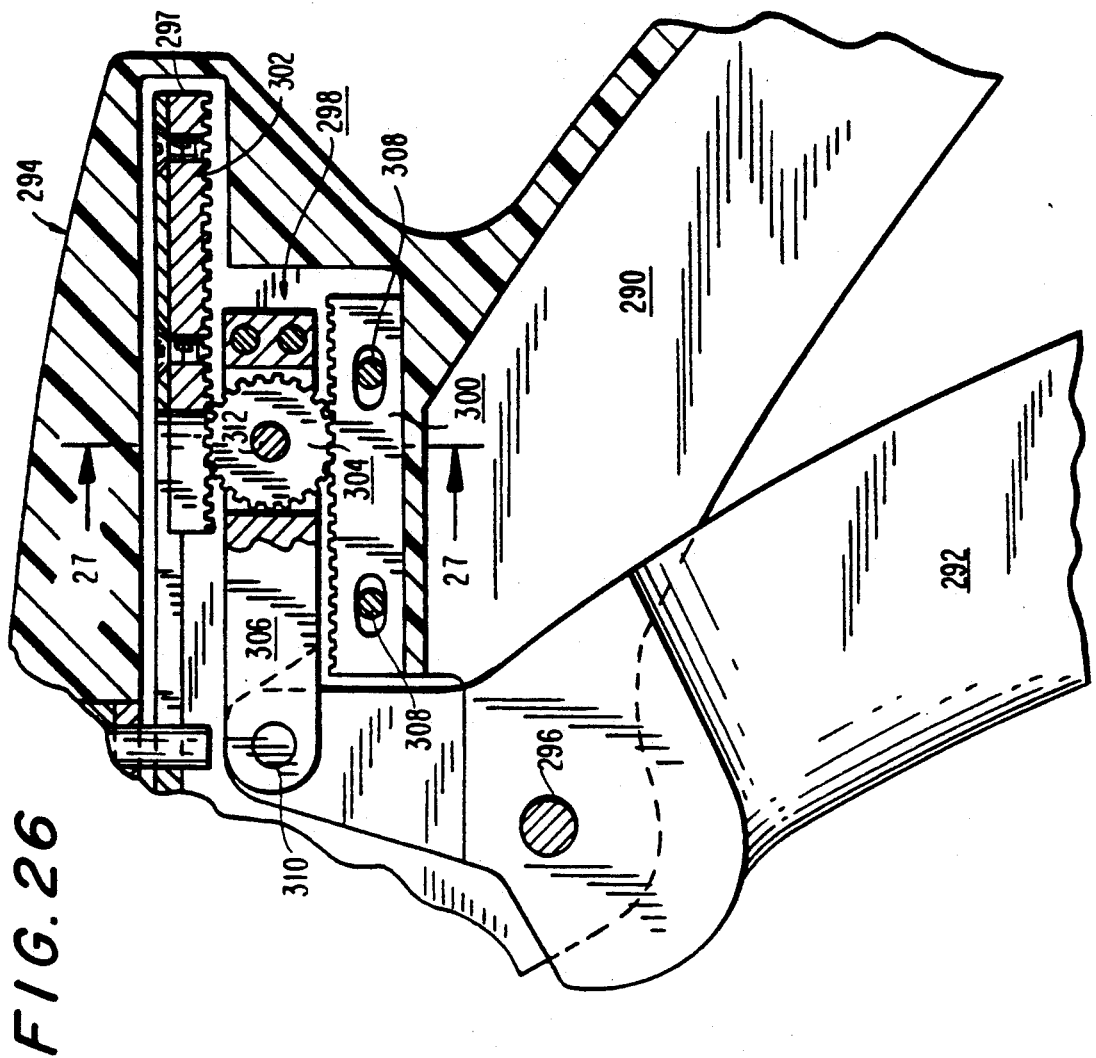
FIG. 26 is a view of an alternative embodiment of a mechanism for closing the pincer jaws and firing the fastener member incorporating a rack and pinion device in a handle section.
Figure 27:
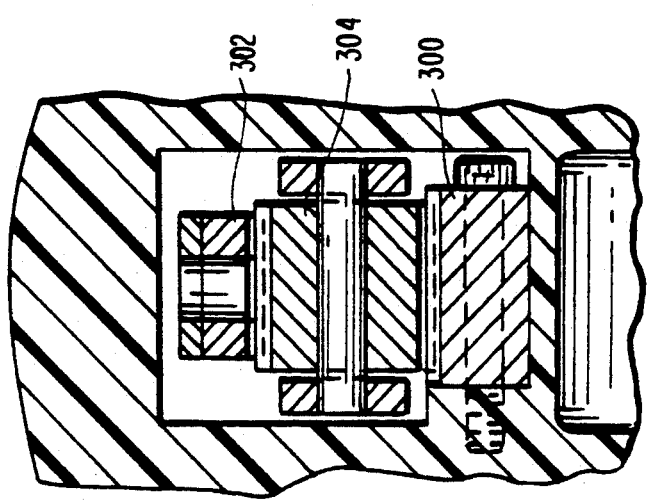
FIG. 27 is a cross-sectional view taken along lines 27—27 of FIG. 26 illustrating the pinion and associated racks.

Referring to FIGS. 26-29, an alternative form of actuating handles are shown which can be utilized with either embodiment of the present invention. Handle 292 is pivotally connected to handle portion 294, and is adapted to pivot about pin 296 from an open position as shown in FIG. 26, toward a closed position adjacent handle 290, as shown in FIG. 29, to move fork 212 to its distal position to thereby close jaws 158 and to move plunger 226 longitudinally to its extended position to discharge fastener 220.

Referring to FIGS. 26-29, rack and pinion assembly 298 translates the pivotal motion of handles 290, 292 to longitudinal motion of fork. Rack and pinion assembly 298 includes a pair of spaced, opposed racks 300, 302, pinion gear 304, and link member 306 which interconnects handle 292 and pinion gear 304. Rack 300 is fixedly secured to handle portion 294 by a pair of cap screws 308 and pinion gear 304 is positioned between racks 300, 302, with its teeth engaged with racks 300, 302. One end of link 306 is pivotally connected via a pin 310 to handle 292 and the other end is attached to pinion gear 304 by a pin 312, about which gear 304 rotates.

Rack 302 is carried within handle portion 294, and is adapted for longitudinal movement therein. As handle 292 is pivoted towards its closed position, link member 306 moves gear 304 distally, as indicated in FIG. 28 by arrow 314. Rack 302 is intermeshed with gear 304 so that rotation of gear 304 causes rack 300 to move longitudinally. As gear 304 moves longitudinally forward along rack 300, gear 304 rotates counterclockwise causing rack 302 to move longitudinally distally. Rack 302 is connectable to fork 212 adjacent its proximal end and transfers longitudinal motion to fork 212 such that fork 212 moves from its proximal position to its distal position.

Spring 297, shown schematically in FIG. 29, attached between the rear end of rack 302 and the rearwardmost extension of handle portion 294, causes rack 302 to move longitudinally rearward when handles 290, 292 are released, thus returning fork 212 to its proximal position. As rack 302 moves longitudinally rearwardly, gear 304 rotates clockwise, and moves proximally rearward along rack 300 causing link 306 to move proximally. Link 306 translates the proximal motion of gear 304 to handle 292, thus returning handle 292 to its open position.

Referring now to FIG. 8, the operative principles of the invention will be described. There is illustrated in phantom the upper surface of skin 316 surrounding an opening 318 such as a wound or surgical incision. The apparatus 10 (or apparatus 148) is positioned such that transverse gripping members 18 are placed generally parallel to the upper surface of the skin, with spaced stabilizers 20, 21 positioned to contact the tissue portions adjacent the proximal and distal ends of griping members 18. Alignment pin 59 is positioned to intersect with opening 318, and apparatus 10 is lowered in the direction of the arrow such that sharp tips of the jaws pierce the skin minimally.

Thereafter, squeezing the handles of the apparatus together moves arms 24 toward each other, closing jaws 12, and causing the sharp tips of the gripping members to intermesh, thus joining the skin portions surrounding opening 318 as shown in FIG. 11, in an at least partially overlapping undulating, or sinusoidal waveform shape, as indicated by phantom lines 56.

At this point, further squeezing of the handles causes plunger 84 to move longitudinally, ejecting the lowermost elongated rod-like fastener longitudinally from the stacked array and into in a position between gripping members 18 and penetrating the overlapped waveform shape to attach the two body tissue portions together (see FIG. 13).

Subsequently, the handles are released, allowing spring 60 to bias arms 24 outwardly, thus returning jaws 12 to their first, open position and allowing their sharp tips to be removed from the body tissue adjacent opening 318. As discussed above, after each fastener is discharged, the next rod-like fastener is biased into the firing chamber segment of chamber 105 under the influence of springs 110.

Depending upon the nature and size of opening 318, one or more fasteners may be discharged in sequence and in adjacent end to end relation, starting at the distalmost segment of the wound and advancing progressively rearwardly to the proximalmost segment of the wound. That is, the apparatus 10 is repositioned rearwardly with its forwardmost stabilizer plate 20 adjacent the rearmost fastener and pin 59 extending into opening 318, and abutting the rearmost end of the previously discharged fastener. Thereafter, squeezing the handles of the apparatus together once again closes jaws 12, causing the sharp tips of the gripping members to intermesh to join the skin segments surrounding opening 318, and causing another fastener to be discharged to penetrate the overlapped waveform shape to attach the two tissue segments. The handles may now be released to return jaws 12 to their first, open position, allowing the sharp tips of jaws 12 to be removed from the body tissue adjacent opening 318.

The apparatus may then be repositioned as necessary in the area adjacent the rearmost inserted fastener to join other segments of opening 318, as described above, until the proximalmost segment of opening 318 is closed. As may be appreciated, the fasteners retain the separate portions of skin in engaged relation such that opening 318 in the skin is prepared for natural permanent healing and adhesion with minimum or no scarring.

The embodiment of FIG. 21 operates in the same manner as described above to close an opening in the body tissue. As is clear, the various handle mechanisms described above can be used to close the jaws and fire the fasteners for either embodiment.

Although the embodiments herein contemplate subcuticular attachment of cutaneous matter, it is within the scope of the invention to apply such rod-like fasteners at subcutaneous levels, i.e. below the epidermis and dermis. As may be further appreciated, the jaws, fork, divider and cartridge may be provided as an assembly which is slid longitudinally into the elongated hollow of the housing, and therein retained by suitable means such as a screw.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical apparatus for attaching at least two portions of body tissue, which comprises:
    a) a pair of opposed jaws;
    b) body tissues engaging means extending from each jaw and facing said opposed jaw and adapted to engage the respective opposed portions of the body tissue such that when said jaws are moved toward each other said engaging means causes said two end portions of the body tissue to be displaced toward each other and engage at the interface so as to assume an irregular shape;
    c) at least one elongated fastener member positioned proximally of said pair of opposed jaws;
    d) actuating means;
    e) means actuated by said actuating means for moving said opposed jaws together toward each other; and
    f) means for directing said at least one elongated fastener member generally medially of the body tissue interface to thereby attach the opposed portions of the body tissue.

2. A surgical apparatus as recited in claim 1, wherein said actuating means comprises at least one handle manually movable to actuate said mechanical means.

3. A surgical apparatus for attaching at least two adjacent end portions of a medium such as cutaneous body tissue, which comprises:
    a) a pair of opposed jaws;
    b) body tissue engaging means extending from each jaw and facing said opposed jaw and adapted to engage the respective opposed portions of the medium such that when said jaws are moved toward each other said engaging means causes said two end portions of the medium to be displaced toward each other and engage at the interface thereof so as to assume an irregular shape whereby a fastening member may be directed generally medially of said medium interface to thereby attach the opposed portions of the medium;
    c) a plurality of rod-like fastener members positioned for sequential ejection generally medially of said jaws when said jaws are moved toward each other; and
    d) manually operable actuating means adapted to move said jaws toward each other for gripping the adjacent end portions of the medium and for ejecting at least one of said fasteners into the medium.

4. The surgical apparatus of claim 3, wherein said manually operable actuating means comprises a pair of handles, at least one handle being pivotally movable toward and away from the other handle.

5. The surgical apparatus of claim 4, wherein initial movement of said at least one handle moves said jaws toward each other and further movement causes ejection of said at least one fastener into the interface of said medium.

6. The surgical apparatus of claim 5, further comprising a plurality of rod-like members carried in a stacked configuration proximally of said jaws, each rod-like member being individually movable to penetrate said body tissue portions when drawn together.

7. A surgical apparatus for attaching two portions of body tissue, comprising:
    a pair of opposed jaws, at least one of said jaws being movable from a first open position spaced apart from the other jaw to a second closed position adjacent the other jaw, each of said jaws having gripping means to engage one portion of the body tissue;

cam means associated with at least one of said jaws;

cam engaging means movable from a first position to a second position to engage said cam means so as to move at least one of said opposed jaws toward the other jaw to said second position to move at least one of the body tissue portions toward the other to a position wherein said body tissue portions are in close approximation; and a rod-like member carried adjacent said jaws, said rod-like member being movable to penetrate said approximated body tissue portions without substantial deformation thereof.

8. The surgical apparatus of claim 7, wherein said apparatus further comprises:

a frame;

a pair of opposed handles extending generally transversely from said frame, at least one of said handles being movable toward the other; and link means interconnecting said handles and said cam engaging means, said link means being movable by the movement of at least one of said handles toward the other, said link means adapted to transfer movement of at least one of said handles to said cam engaging means to move said cam engaging means from its first position to its second position.

9. The surgical apparatus of claim 7, wherein said apparatus further comprises:

a frame;

a pair of opposed handles extending generally rearwardly from said frame and movable toward and away from each other; and a parallelogram shaped transmission pivotally interconnected at opposite ends thereof to said handles so that the movement of said handles toward and away from each other allows said parallelogram to expand and contract, said transmission interconnecting with said cam engaging means to translate the motion of said handles toward each other to move said cam engaging means from its first position to its second position.

10. The surgical apparatus of claim 7, wherein said apparatus further comprises:

a frame;

a pair of opposed handles extending generally transversely from said frame, at least one of said handles being movable toward and away from the other; and a rack carried by said frame and movable longitudinally by the rotative motion of a pinion, said cam engaging means being connected with said rack for longitudinal motion therewith, said pinion being rotated by the movement of said handle toward the other to move said rack longitudinally to move said cam engaging means from its first position to its second position.

11. The surgical apparatus of claim 7, wherein said gripping members of said jaws extend transversely from said jaws.

12. The surgical apparatus of claim 11, wherein said jaws are adapted to position said body tissue portions laterally therebetween in a partially overlapping configuration.

13. The surgical apparatus of claim 12, wherein said rod-like member is movable transversely across said jaws to penetrate said overlapping configuration.

14. The surgical apparatus of claim 7, wherein cam means defining a cam face is included with each jaw, and wherein said cam engaging means is a fork having tines adjacent said cam faces, said fork being carried by said frame for movement from a first to a second position, said tines being engagable with said cam faces as said fork is moved toward its second position to move said jaws toward their closed position by the movement of said fork to its second position.

15. The surgical apparatus of claim 14, wherein said fork is longitudinally movable to a third distal position to move said rod-like members.

16. The surgical apparatus of claim 15, wherein said second position of said fork is intermediate said first and third positions.

17. The surgical apparatus of claim 7, wherein said apparatus further comprises plunger means engagable with at least one of said rod-like members and movable from a first position to a second position to move said rod-like member into said body tissue portions.

18. The surgical apparatus of claim 17, wherein said cam engagable means is movable from its second position to a third position to move said plunger means to its second position.

19. The surgical apparatus of claim 18, wherein said second position of said cam engagable means is intermediate said first and third positions of said cam engagable means.

20. The surgical apparatus of claim 19, wherein said apparatus further comprises:

a pair of opposed handles extending generally transversely from said frame, at least one of said handles being movable toward the other; and link means interconnecting said handles and said cam engaging means, said link means being movable by the movement of at least one of said handles toward the other, said link means transferring the movement of at least one of said handles to said cam engaging means to move said cam engaging means from its first position to its third position.

21. The surgical apparatus of claim 18, wherein said plunger means includes an elongated plunger rod longitudinally movable from a first position to a second position by a further movement of said fork from its second position to a third position.

22. The surgical apparatus of claim 21, wherein said plunger rod engages against the lowermost rod-like member as said plunger rod is moved to its second position.

23. A surgical apparatus for attaching two portions of cutaneous body tissue, comprising:

a pair of opposed jaws, at least one of said opposed jaws being movable by manually operable transmission means from a first open position spaced apart from said other jaw to a second closed position adjacent said other jaw, each of said jaws having a member to engage one portion of the body tissue, said jaws having means for holding the portions of body tissue in approximation when moved to their closed position; and means adjacent said jaws for ejecting an elongated rod-like fastener into a path extending between said closed jaws so as to penetrate the cutaneous body tissue without substantial deformation of said rod-like fastener.

24. The surgical apparatus of claim 23, wherein said jaws are configured to hold said portions of body tissue in at least partially overlapping waveform.

25. The surgical apparatus of claim 24, further comprising means for altering the path of said ejected rod-like fastener.

26. The surgical apparatus of claim 25, wherein said means for altering the path of said ejected rod-like fastener comprises an arcuate bore.

27. The surgical apparatus of claim 24, wherein said non-linear path is arcuate.

28. The surgical apparatus of claim 23, wherein said means for holding the portions of body tissue in approximation comprises a pair of spaced gripping members on one of said jaws, and at least one gripping member positioned on the other of said jaws which intersects at least partially between said pair of spaced gripping members when said jaws are moved to their closed position.

29. The surgical apparatus of claim 23, wherein said fastener ejecting means comprises an elongated rod movable longitudinally to eject said rod-like fastener into said path.

30. A surgical apparatus for attaching at least two adjacent end portions of a medium such as cutaneous body tissue, which comprises:
   a) a pair of opposed jaws;
   b) body tissue engaging means extending from each jaw and facing said opposed jaw and adapted to engage the respective opposed portions of the medium such that when said jaws are moved toward each other said engaging means causes said two end portions of the medium to be displaced toward each other and engage at the interface so as to assume an irregular shape;
   c) at least one elongated fastener positioned proximally of said pair of opposed jaws;
   d) mechanical means for moving said jaws toward each other;
   e) manually operable actuating means for actuating said mechanical means to move said jaws toward each other; and
   f) means for directing said at least one elongated fastener member generally medially of the body tissue interface to thereby attach the opposed portions of the body tissue.

31. The surgical apparatus of claim 30, wherein said actuating means comprises a pair of handles.

32. A surgical fastening apparatus for attaching two adjacent portions of cutaneous body tissue comprising:
   at least one elongated rod-like fastener defining a generally longitudinal axis;
   pusher means for directing said elongated fastener in a first longitudinal direction and thereafter in a second longitudinal direction prior to insertion into the body tissue.

33. The surgical apparatus of claim 32, wherein said ejection means comprises an elongated rod longitudinally movable from a first position to a second position to eject said elongated fastener.

34. The surgical apparatus of claim 32, wherein said means for altering the direction is an arcuate bore through which said elongated fastener passes.

35. In a surgical apparatus for attaching at least two adjacent end portions of body tissue, the improvement in combination therewith comprising:
   means for holding the adjacent end portions of tissue in approximation;
   actuating means;
   means actuated by said actuation means for moving said tissue holding means to approximate and hold the end portions of body tissue; and
   means for advancing an elongated rod-like fastener member defining a longitudinal axis along a first longitudinal path and thereafter along a second longitudinal path angled relative to said first longitudinal path so as to direct said fastener member into the end portions and attach the end portions together.

36. A surgical apparatus for attaching two portions of cutaneous body tissue, comprising:
   a pair of opposed jaws, at least one of said opposed jaws being movable from a first open position spaced apart from the other jaw to a second closed position adjacent the other jaw, each of said jaws engaging one portion of the body tissue when moved to said second position, said jaws having means for holding the portions of body tissue in an adjacent, at least partially overlapping waveform;
   means adjacent said jaws for ejecting an elongated rod-like fastener into a path extending transversely between said closed jaws and intersecting longitudinally with said overlapping waveform to attach the portions of body tissue; and
   a pair of spaced tissue stabilizer means positioned adjacent said jaws and in close approximation thereto when said jaws are moved to their closed position, said stabilizer means being positioned along the axis of said path extending transversely between said closed jaws and positioned to contact body tissue portions adjacent the ends of said overlapping waveform when said jaws are moved to their closed position to stabilize said jaws in a position suitable for attachment of the portions of body tissue.

37. The surgical apparatus of claim 36, wherein said means for holding the portions of body tissue in an overlapping waveform comprises a pair of spaced gripping members on one of said jaws, and at least one gripping member positioned on the other of said jaws which is positioned between said first mentioned pair of spaced gripping members when said jaws are moved to their closed position.

38. The surgical apparatus of claim 37, wherein said ejecting means comprises an elongated rod movable longitudinally to eject said rod-like fastener into said path intersecting longitudinally with said overlapping waveform.

39. A surgical apparatus for attaching two portions of cutaneous body tissue, comprising:
   a frame;
   a pair of opposed jaws carried by said frame, at least one of said opposed jaws being movable from a first open position spaced apart from the other jaw to a second closed position adjacent the other jaw, each of said jaws having a member to engage one portion of the body tissue when moved to said second position;
   a ramp included with at least one of said opposed jaws and positioned adjacent said frame;
   roller means rollable along said frame from a first position to a second position between said ramp and said frame, said roller means rolling along said ramp and said frame to urge at least one of said opposed jaws laterally towards the other jaw to said second position to move said body tissue portions toward one another to a position wherein said two body tissue portions are drawn together in close approximation; and a rod-like member carried proximally of said jaws, said rod-like member being movable to penetrate said body tissue portions when drawn together in close approximation.

40. A surgical apparatus for attaching two end portions of body tissue which comprises:

a pair of jaws movable toward each other to a closed position;

a pair of spaced gripping members on one of said jaws extending generally toward the other jaw;

at least one gripping member positioned on the other jaw extending generally toward the opposite jaw at a position at least partially between said pair of spaced gripping members when said jaws are moved to their closed positions;

means for discharging an elongated rod-like fastener movable longitudinally to discharge said rod-like fastener into said body tissue; and manual actuating means adapted to actuate mechanical transmission means for moving said pair of jaws toward each other.

41. A method of attaching two portions of cutaneous body tissue with an apparatus having means for holding the two portions of body tissue together and actuating means adapted to actuate transmission means for displacing said body tissue holding portions toward each other, comprising the steps of:

manually gripping said actuating means and causing said actuating means to actuate said transmission means so as to move said body tissue holding means toward each other;

overlapping the two portions of body tissue in an adjacent, at least partially overlapped waveform;

ejecting an elongated rod-like fastener along a vector which intersects longitudinally with the overlapped waveform; and penetrating the overlapped waveform longitudinally with the elongated rod-like fastener to attach the two portions of cutaneous body tissue together.

42. A method of attaching two portions of cutaneous body tissue, comprising the steps of:

overlapping the distalmost segments of two end portions of body tissue in an adjacent, at least partially overlapped waveform by moving a pair of jaws toward each other;

penetrating the overlapped waveform longitudinally with an elongated rod-like fastener ejected along a vector that intersects longitudinally with the overlapped waveform to attach the segments of cutaneous body tissue together;

positioning of said jaws adjacent the posterior end of said elongated rod-like fastener holding the segments of body tissue together to locate the jaws in a position to overlap the adjacent segments;

overlapping the distal body tissue segments adjacent the attached segments in an adjacent, at least partially overlapped waveform by moving a pair of jaws toward each other;

penetrating the overlapped waveform longitudinally with an elongated rod-like fastener ejected along a vector which intersects longitudinally with the overlapped waveform to attach the segments of cutaneous body tissue together; and repeating the steps of positioning, overlapping the distal segments adjacent the attached segment and penetrating the overlapped waveform until the end portions of body tissue are attached.

43. A method of attaching two portions of body tissue comprising:

a) positioning an apparatus adjacent an opening between the body tissue portions;

b) actuating said apparatus to bring the two positions of body tissue into adjacent relation and inserting a first rod-like fastener into a region formed by the abutment of the two body tissue portions whereby said fastener is positioned longitudinally with respect to the opening;

c) placing said apparatus in position adjacent the inserted fastener;

d) inserting another rod-like fastener; and e) repeating steps c and d to place a linear row of fasteners one at a time along the length of the opening.

44. A surgical apparatus for attaching at least two adjacent end portions of a medium such as cutaneous body tissue, which comprises:

a) a pair of opposed jaws;

b) body tissue engaging means extending from each jaw and facing said opposed jaw and adapted to engage the respective opposed portions of the medium such that when said jaws are moved toward each other said engaging means causes said two end portions of the medium to be displaced toward each other and engage at the interface so as to assume an irregular shape;

c) at least one elongated fastener member positioned proximally of said pair of opposed jaws, said fastener member defining a generally longitudinal axis;

d) mechanical means for moving said jaws toward each other;

e) manually operable actuating means for actuating said mechanical means to move said jaws toward each other; and f) means for directing said at least one elongated fastener member generally in a direction generally in line with said longitudinal axis of said fastener to thereby attach the opposed portions of the body tissue.

* * * * *